US007011939B2

(12) United States Patent
Trumbull et al.

(10) Patent No.: US 7,011,939 B2
(45) Date of Patent: *Mar. 14, 2006

(54) APPARATUS AND METHOD FOR ELECTROPHYSIOLOGICAL TESTING

(75) Inventors: Jonathan D. Trumbull, Zion, IL (US); Daniel C. Bertrand, Geneva (CH); Clark A. Briggs, Libertyville, IL (US); David G. McKenna, McHenry, IL (US); Eugene S. Maslana, Morton Grove, IL (US); David P. Blanchard, Kenosha, WI (US); Jeffrey Y. Pan, Lake Forest, IL (US); Peter Bojan, Grayslake, IL (US); Thomas A. Nemcek, Crystal Lake, IL (US)

(73) Assignee: Abbott Laboratories, Abott Park, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/790,871

(22) Filed: Feb. 23, 2001

(65) Prior Publication Data

US 2001/0029320 A1  Oct. 11, 2001

Related U.S. Application Data

(63) Continuation-in-part of application No. 09/532,686, filed on Mar. 22, 2000.

(51) Int. Cl.
  *C12Q 3/00* (2006.01)
(52) U.S. Cl. .................. 435/3; 435/33; 435/286.4; 435/287.1; 435/287.3
(58) Field of Classification Search .............. 435/29, 435/32, 33, 30, 187.1, 286.2, 286.4, 286.5, 435/287.3, 288.3, 6, 4, 3, 287.4
See application file for complete search history.

(56) References Cited

U.S. PATENT DOCUMENTS

| 3,696,805 | A | | 10/1972 | Sweeten et al. |
|---|---|---|---|---|
| 3,998,215 | A | | 12/1976 | Anderson et al. |
| 5,139,744 | A | | 8/1992 | Kowalski |
| 5,282,149 | A | * | 1/1994 | Grandone et al. ............ 702/19 |
| 5,390,238 | A | | 2/1995 | Kirk et al. |
| 5,496,697 | A | * | 3/1996 | Parce et al. ................... 435/29 |
| 5,511,553 | A | | 4/1996 | Segalowitz |
| 5,670,113 | A | * | 9/1997 | Akong et al. ................. 422/63 |
| 6,048,722 | A | | 4/2000 | Farb et al. |
| 6,268,121 | B1 | * | 7/2001 | Takeshita et al. ........... 204/400 |
| 6,383,813 | B1 | * | 5/2002 | Baxter et al. ............ 435/285.1 |
| 6,488,829 | B1 | * | 12/2002 | Schroeder et al. ..... 204/403.01 |

FOREIGN PATENT DOCUMENTS

| WO | WO 97/17426 | | 5/1997 |
|---|---|---|---|
| WO | WO-98/50791 A1 | * | 11/1998 |
| WO | WO 98/52047 | | 11/1998 |

OTHER PUBLICATIONS

W. Stuhmer, "Electrophysiologic Recordings from Xenopus Oocytes", Methods in Enzymology, vol. 293, Academic Press (1998), pp. 280-300.
Akaike, N., et al., "Concentration Clamp Study of y-Aminobutyric Acid-Induced Chloride Current Kinetics in Frog Sensory Neurones", Journal of Physiology (1986), vol. 379, pp. 171-185.
Madeja, M., et al., "A concentration—clamp system allowing two-electrode voltage-clamp investigations in oocytes of *Xenopus laevis*", Journal of Neuroscience Methods, vol. 38 (1991), pp. 267-269.
Madeja, M., et al., "Improvement and testing of a concentration-clamp system of oocytes of *Xenopus laevis*", Journal of Neuroscience Methods, vol. 63 (1995), pp. 211-213.
Shih, T., et al., "High -Level Expression and Detection of Ion Channels in *Xewnoopus Oocytes*", Expression Systems, Academic Press (1998), pp. 529-556.
Weber, "Ion currents of *Xenopus laevis oocytes*:State of the Art", Biochimica et Biophysica Acta 1421 (1999), pp. 213-233.
Brochure—Oocyte Testing Carousel System (OTC-20) from ALA Scientific Instruments (No date provided).

Brochure—Solution Exchange System (BPS-8) from ALA Scientific Instruments (No date provided).
Crystallization Research Tools, Hampton Research, vol. 9, No. 1, 1999, pp. 50-53.
International Search Report (Apr. 5, 2002).
PCT Written Opinion (Jun. 20, 2002).

* cited by examiner

*Primary Examiner*—Willaim H. Beisner
(74) *Attorney, Agent, or Firm*—David L. Weinstein

(57) ABSTRACT

A method and apparatus for running a plurality of tests concurrently to obtain data relating to the electrophysiological properties of receptors and channels in biological membranes of test subjects, such as, for example, *Xenopus* oocytes. The invention further provides software for controlling, acquiring, and recording data relating to electrophysiological properties of receptors and channels in biological membranes of test subjects, such as, for example, oocytes. This invention increases the throughput rate for experiments and assays employing receptors and ion channels expressed in biological membranes of test subjects, such as, for example, oocytes. In the case of an oocyte, these receptors and channels may be natively expressed (endogenous), may be placed into the oocyte (exogenous), or may be expressed from other RNA or DNA previously placed into the oocyte (exogenous).

The invention provides a means for a sole researcher to operate a plurality of electrophysiological test stations in the time and space conventionally required by a single electrophysiological test station. The invention automates these stations and provides a means for a sole individual to perform large sets of experiments that would be physically and mentally exhausting in the absence of this invention. In addition, this invention provides efficient database and data analysis software integrated with the data acquisition software, thereby increasing the user's data-handling productivity to keep pace with the augmented data generation capacity.

28 Claims, 16 Drawing Sheets

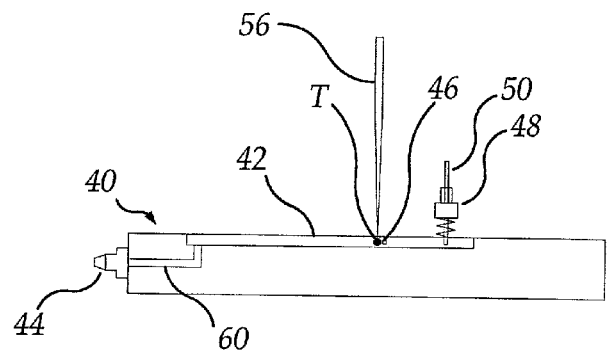
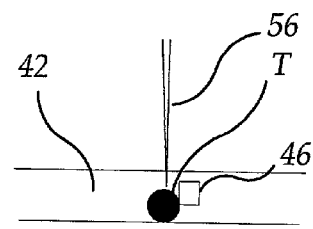
FIG. 4A    FIG. 4B
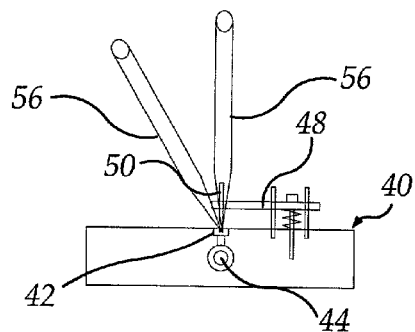
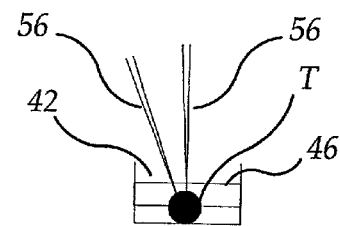
FIG. 4C    FIG. 4D
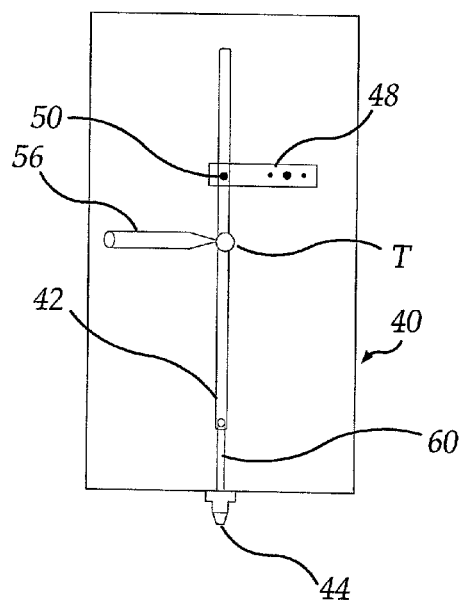
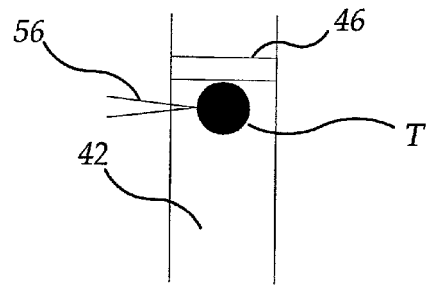
FIG. 4E    FIG. 4F

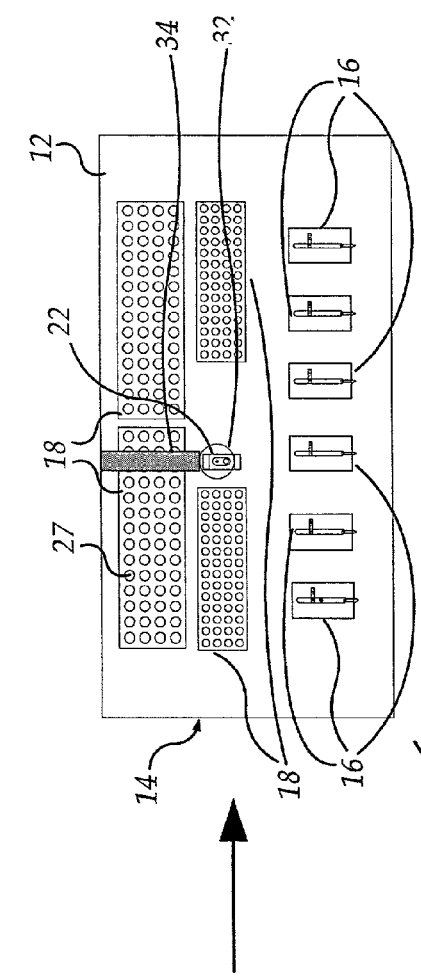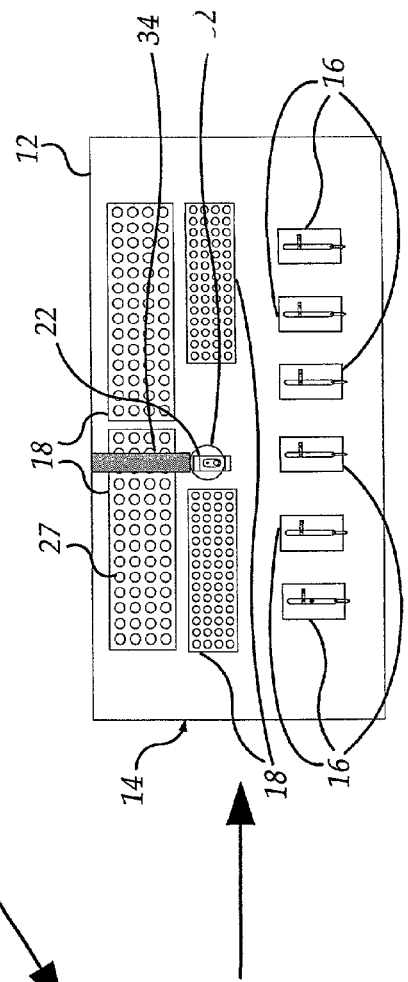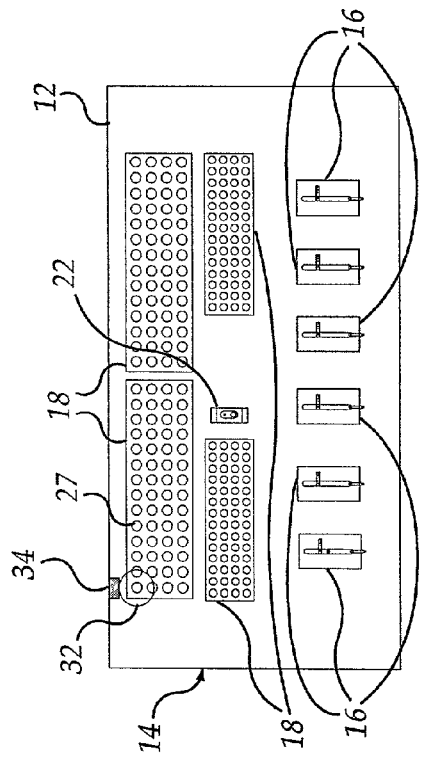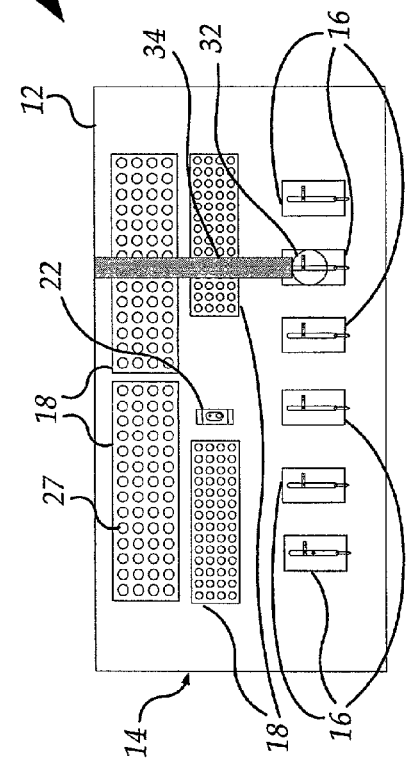

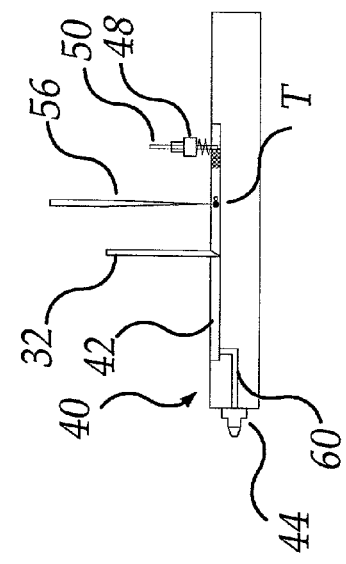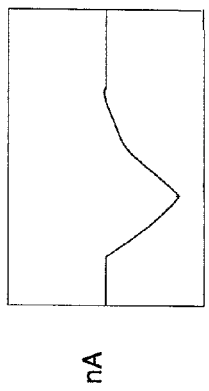
FIG. 6C
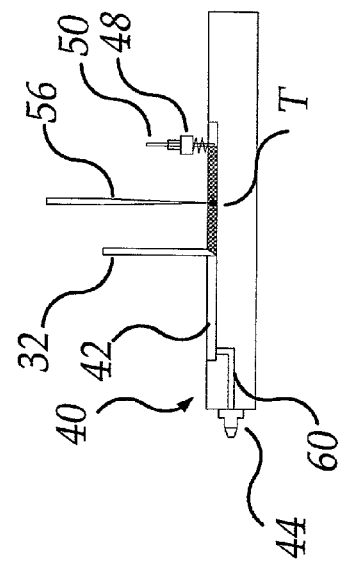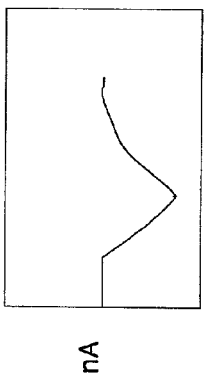
FIG. 6B
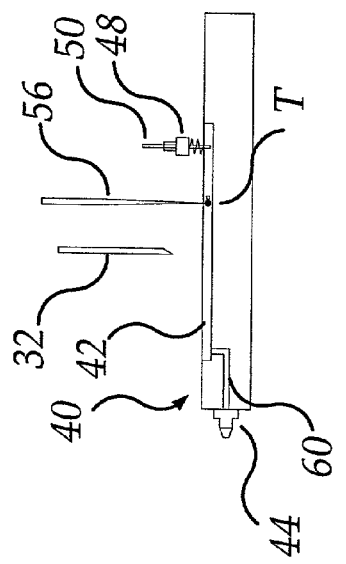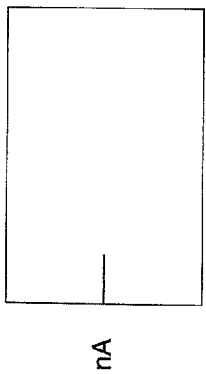
FIG. 6A

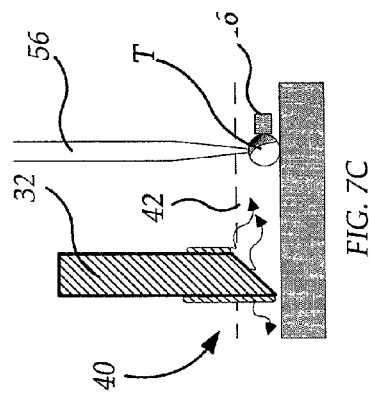
FIG. 7A
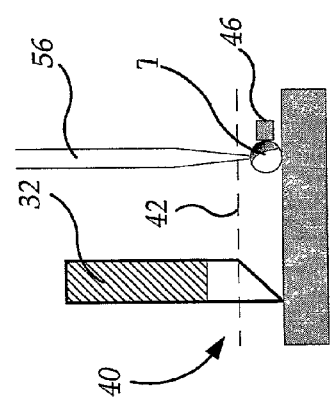
FIG. 7B
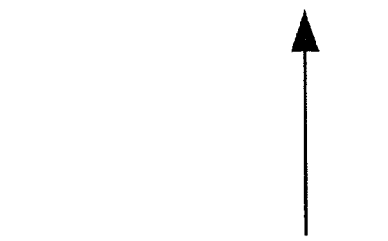
FIG. 7C
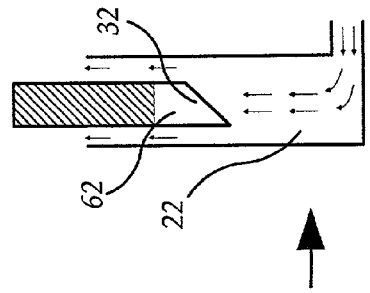
FIG. 7D
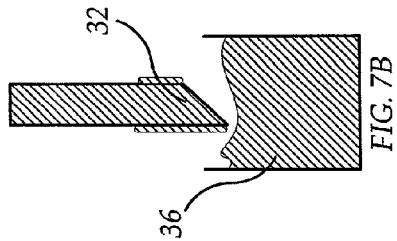
FIG. 7E
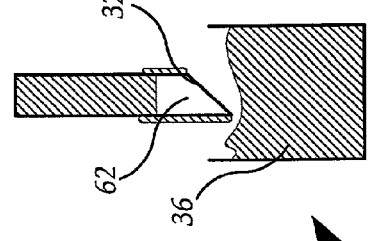
FIG. 7F
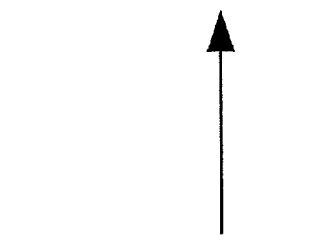
FIG. 7G
FIG. 7H

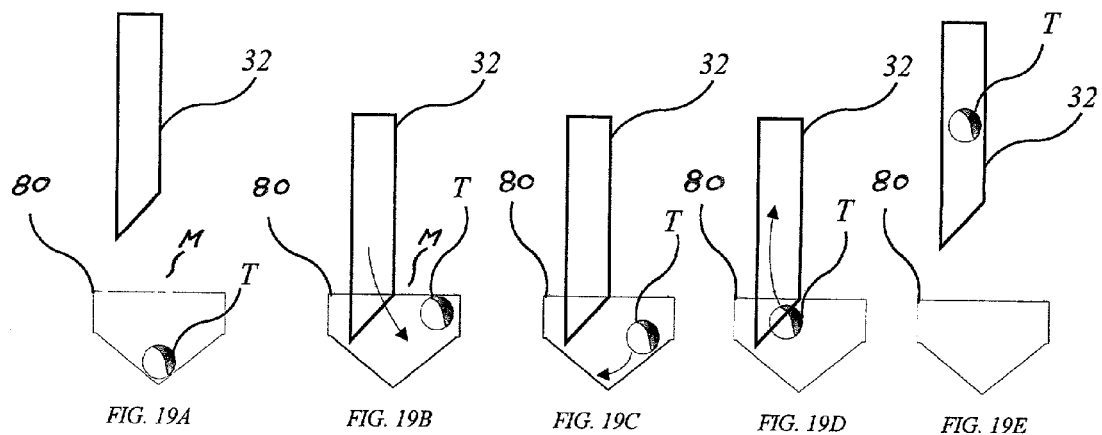
FIG. 19A  FIG. 19B  FIG. 19C  FIG. 19D  FIG. 19E
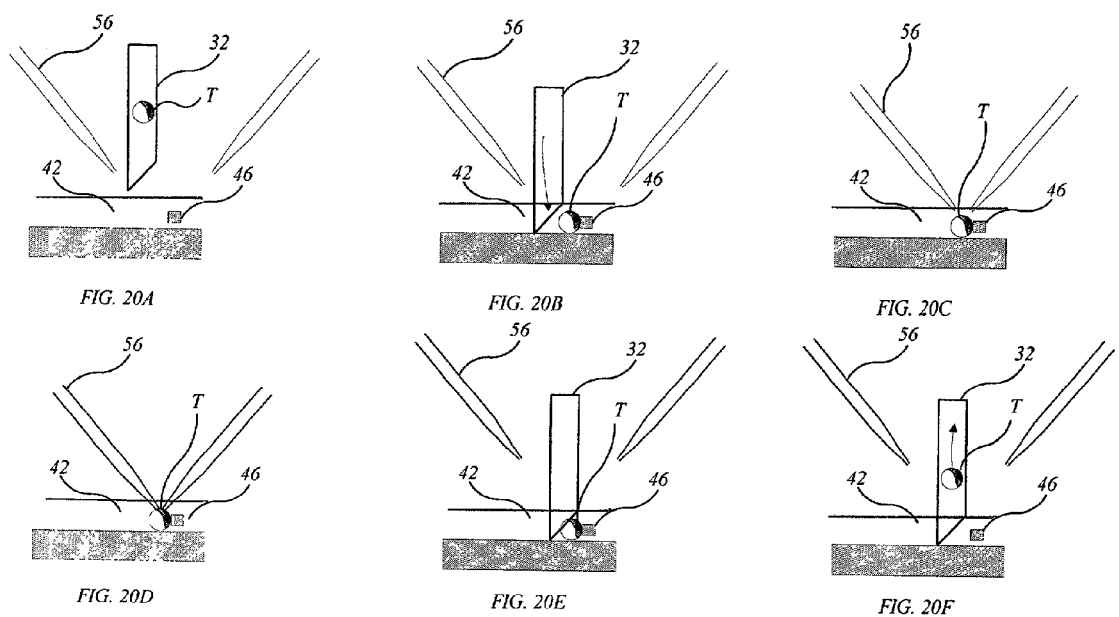
FIG. 20A  FIG. 20B  FIG. 20C
FIG. 20D  FIG. 20E  FIG. 20F

APPARATUS AND METHOD FOR ELECTROPHYSIOLOGICAL TESTING

This application is a continuation-in-part of U.S. Ser. No. 09/532,686, filed Mar. 22, 2000.

BACKGROUND OF THE INVENTION

1. Field of the Invention

This invention relates to electrophysiological testing of biological samples. In particular, this invention relates to electrophysiological testing of agonists, antagonists, modulators, and other molecular species to determine their effect upon ion channels, electrical potential of cell membrane, and electrical currents through cell membranes.

2. Discussion of the Art

Electrophysiological methods provide the best and, often, the only available approach for studying and testing responses of ion channels of cell membranes. Such channels, which control the flow of ions across cell membranes and regulate the electrical potential of cells, are critically important for the proper functioning of plant and animal cells. Well-known examples of this are found in the nervous, muscle, cardiovascular, endocrine, and immune systems. Understanding the actions of substances that regulate ion channels (e.g., neurotransmitters, hormones, alkaloids, toxins, alcohols, and anesthetics) and discovering novel therapeutics that act through ion channels are important enterprises that are dependent upon electrophysiological approaches and the testing of ion channels in biological membranes. However, conventional methods have been hampered by low throughput, even in facile models such as transfected *Xenopus* oocytes.

The simplest method of increasing the rate of data collection is to multiply the number of conventional electrophysiological testing stations and the personnel needed to operate them. However, such actions increase costs for equipment, floor space, overhead, and personnel. Because of the initial cost of a conventional workstation, the floor space required, and the omnipresent difficulties in recruiting and retaining qualified electrophysiologists, this approach is not ideal.

Some researchers have used a manifold system, wherein many tubes of solutions are brought into a single chamber, with the individual tubes being controlled by solenoid valves (which can operate under the control of a computer). See, for example, ValveBank8 Perfusion System, commercially available from AutoMate Scientific, Inc. (Oakland, Calif.). This approach allows automated experiments to be performed, but still requires tedious, manual priming operations to be performed for each compound at each concentration. In addition, the duration of a given experiment is dominated by the duration of flow channel cleaning and duration of receptor recovery, and not duration of data collection. Thus, the system is idle for most of the experiment, effectively wasting resources. Increasing throughput would require complete system replication.

The "OTC-20" instrument (ALA Scientific Instruments, Westbury, N.Y.) utilizes a 20-sample carousel and provides low dead volume with random access to reagents for a single *Xenopus* oocyte. This system employs a movable, closed oocyte flowcell having electrodes integrated therewith. This flowcell has a bottom orifice that allows it to be dipped into a Petri dish containing the reagents needed for the experiment. A rotating carousel allows random access to Petri dishes containing solutions of the compound being tested. However, the system is limited to one oocyte and only 20 test samples at a time. The crude method of random access prevents the reagent vessels common in the pharmaceutical industry from being used and severely limits the number of samples that can be tested in one operation. Loading of the oocytes into the flowcell is also difficult and not amenable to high throughput. This approach also suffers from the two difficulties previously discussed, namely the apparatus spends the majority of the experiment waiting for the oocyte to recover, and increases in throughput require multiple systems.

In a conventional method of data analysis, data from each response is stored as a coded file, the relevant information existing as text tags in the file (see, for example, Clampex, available from Axon Instruments, incorporated herein by reference). To construct a dose response curve, these files must be analyzed individually by means of a separate software program (see, for example, Clamp-Fit, available from Axon Instruments, incorporated herein by reference). The results of each of these separate analyses are normalized to similar measurements of the responses from reference (control) agonist. In general, a simple normalization scheme is used because of the tedious nature of the operation. The responses at the required doses are averaged for an individual test subject and a table of results is constructed. A series of tables is constructed for the same test material on a varying number of test subjects. This series of tables is then imported into a curve-fitting package (see, for example, Prism, available from GraphPad, incorporated herein by reference), where the appropriate parameters are extracted. These parameters are used to create another series of table entries to be exported into a database for long-term storage and integration with other data. All of these steps are manual "cut and paste" operations, employing several software products. These steps are not only very time-consuming, but also susceptible to error due to their manual and highly repetitive nature.

Thus, there is a clear need for methods and devices to augment throughput in electrophysiological data acquisition and analysis, thereby increasing productivity.

SUMMARY OF THE INVENTION

This invention provides a method and apparatus for running a plurality of tests concurrently to obtain data relating to the electrophysiological properties of receptors and channels in biological membranes of test subjects, such as, for example, *Xenopus* oocytes. The invention further provides software for controlling, acquiring, and recording data relating to electrophysiological properties of receptors and channels in biological membranes of test subjects, such as, for example, oocytes. This invention increases the throughput rate for experiments and assays employing receptors and ion channels expressed in biological membranes of test subjects, such as, for example, oocytes. In the case of an oocyte, these receptors and channels may be natively expressed (endogenous), may be placed into the oocyte (exogenous), or may be expressed from other RNA or DNA previously placed into the oocyte (exogenous).

In one aspect, this invention provides a method wherein a plurality of test subjects having receptors and channels in biological membranes, such as, for example, oocytes, are subjected to a series of test materials, such as, for example, compounds, which are delivered by a sampling station. The electrical responses of the test subjects are recorded by a data acquisition system and logged into a database. The throughput of the method is increased, relative to that of methods previously known, by collecting data in sequence from each test subject, while the remaining test subjects are recovering for the next application of a test material. Because the recovery time of a test subject, such as receptors or channels in a *Xenopus* oocyte, exceeds the time required for application of a test material, the runs involving the test subjects are carried out essentially concurrently, and there is no adverse effect upon the quality of data.

Automated control of the sampling station allows random access to many test materials that may be applied to a set of test subjects without the need for intervention by an operator (after the initial setup) and without the need for priming a plurality of valves of a manifold. Automated control allows assays to be run without the need for large quantities of the test material. Consumption of a test material is also reduced by a significant reduction in the dead volume in both the sampling station and the flow channel, as compared with conventional implementations known in the art. The costs attributable to time and material can be further reduced by testing compounds as an agonist, an antagonist, and a modulator within the same protocol.

In another aspect, the invention provides an apparatus comprising a plurality of recording stations for holding a plurality of test subjects; a sampling station for dispensing test materials into the recording stations; means for controlling experimental conditions; means for recording and measuring ion channel responses; means for collecting data; means for storing data in a database; and means for analyzing experimental results.

The method and apparatus of this invention multiplies the effectiveness and productivity of a single operator and reduces the consumption of valuable test materials by 1–2 orders of magnitude. It provides a plurality of recording stations in the space previously occupied by one recording station, increasing productivity without increasing floorspace or other building overhead. It further increases productivity by providing an integrated means for analyzing recorded data at the same time new data is being acquired by the automated system.

The present invention provides a means for a sole researcher to operate a plurality of electrophysiological test stations in the time and space conventionally required by a single electrophysiological test station. The invention automates these stations and provides a means for a sole individual to perform large sets of experiments that would be physically and mentally exhausting in the absence of this invention. In addition, this invention provides an efficient database and data analysis software integrated with the data acquisition software, thereby increasing the user's data-handling productivity to keep pace with the augmented data generation capacity. Thus, this invention will enhance the rate by which new knowledge can be gained in basic research, and novel drugs can be found in pharmaceutical discovery.

BRIEF DESCRIPTION OF THE DRAWINGS

FIG. 4A is a schematic diagram illustrating a side view in elevation of a single flowcell of the apparatus of this invention.

FIG. 4B is a schematic diagram, greatly enlarged, illustrating a side view in elevation of a test subject situated in a flowcell of the apparatus of this invention.

FIG. 4C is a schematic diagram illustrating a front view in elevation of a single flowcell of the apparatus of this invention.

FIG. 4D is a schematic diagram, greatly enlarged, illustrating a front view in elevation of a test subject situated in a flowcell of the apparatus of this invention.

FIG. 4E is a schematic diagram illustrating a plan view of a single flowcell of the apparatus of this invention.

FIG. 4F is a schematic diagram, greatly enlarged, illustrating a plan view of a test subject situated in a flowcell of the apparatus of this invention.

FIGS. 5A, 5B, 5C, and 5D are top plan views illustrating a sequence of steps for processing a sample.

FIGS. 6A, 6B, and 6C are side views illustrating a sequence of steps for processing a sample. Below each view is a graph illustrating the relationship of current measured as a function of time for each of the steps in the sequence.

FIGS. 7A, 7B, and 7C are schematic views illustrating a sequence of steps for application of a test material by an applicator when the applicator has not been washed.

FIGS. 7D, 7E, 7F, 7G, and 7H are schematic views illustrating a sequence of steps for application of a test material by an applicator when the applicator has been washed according to the method of this invention.

FIGS. 19A, 19B, 19C, 19D, and 19E are schematic views illustrating a sequence of steps for loading a *Xenopus* oocyte into an applicator.

FIGS. 20A, 20B, 20C, 20D, 20E, and 20F are schematic views illustrating a sequence of steps for loading a *Xenopus* oocyte into a flowcell and unloading a *Xenopus* oocyte from a flowcell.

DETAILED DESCRIPTION

Figure 1:
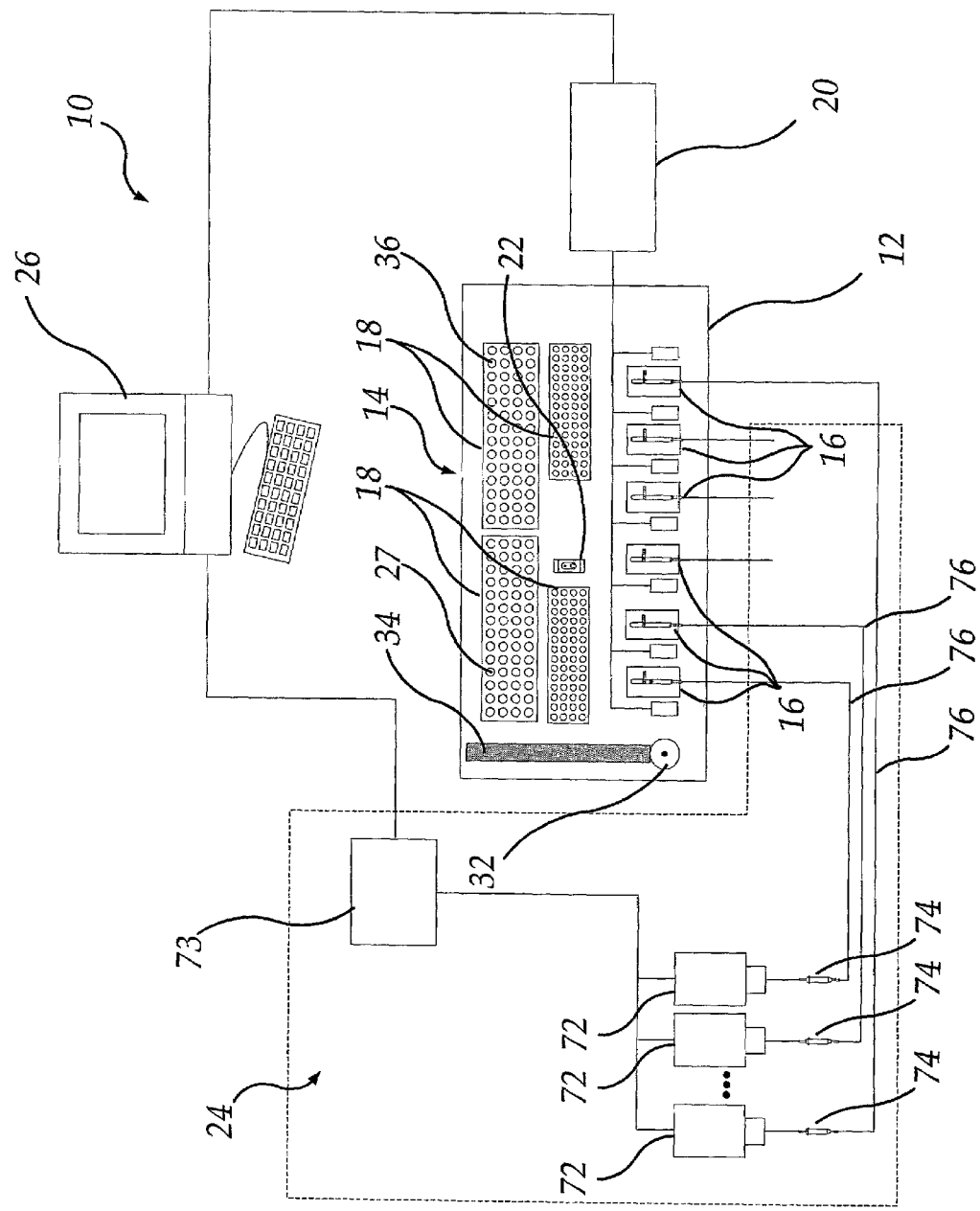
FIG. 1 is a schematic diagram illustrating an arrangement of the apparatus of this invention.
Figure 2:
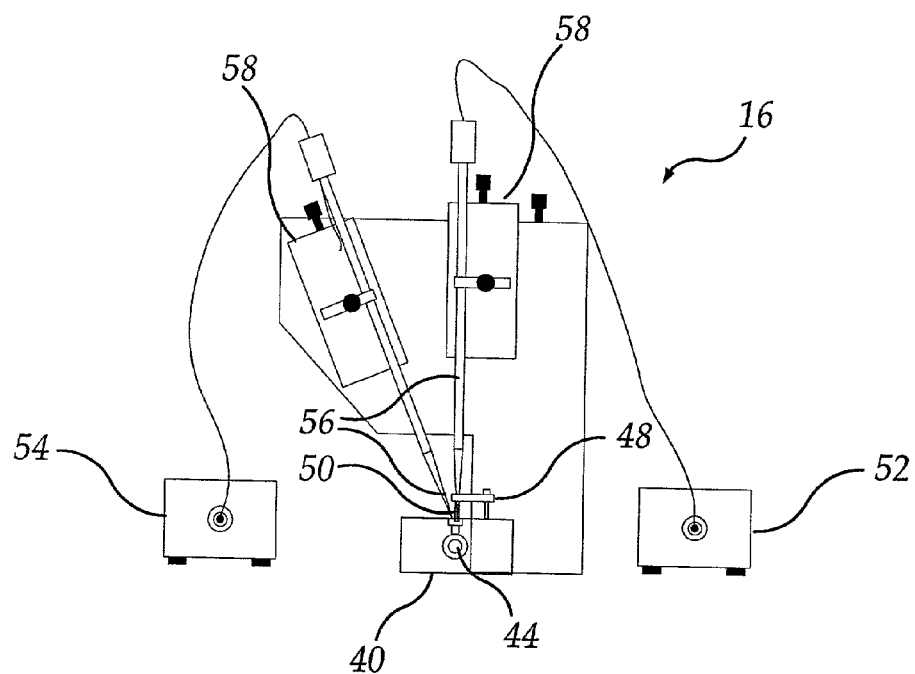
FIG. 2 is a schematic diagram illustrating a front view in elevation of a single recording station of the apparatus of this invention.
Figure 3:
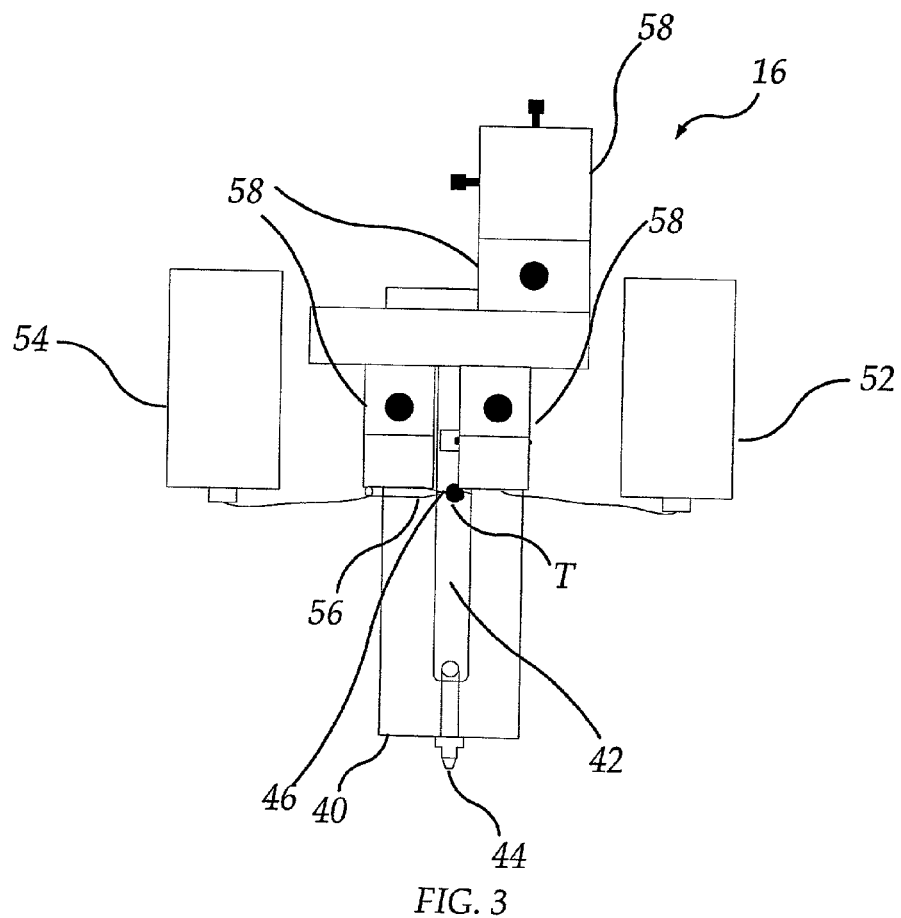
FIG. 3 is a schematic diagram illustrating a top plan view of a single recording station of the apparatus of this invention.

As used herein, the expression "ligand-gated ion-channel" means a transmembrane protein unit that acts as a gate for one or more charged species to move into or out of a cell. The state of the ligand-gated ion-channel is controlled primarily by the binding of small molecules (ligands) to either the protein unit itself or to a related area. Similarly, the expression "voltage-gated ion channel" refers to an ion channel that is controlled primarily by a voltage gradient, which gradient is generally similar to the range of electrical potentials observed in biological cells. The expression "voltage clamping" means a technique for measuring the flow of current through a cell membrane by holding its voltage constant. See, for example, "Electrophysiological Recordings from *Xenopus* Oocytes", Walter Stuhmer, *Methods in Enzymology*, Vol. 293, Academic Press (1998). The expression "test subject" means the object that is to be subjected to a test material. In clinical trials, humans are the test subjects. In the present invention, representative examples of test subjects include, but are not limited to, a biological cell, such as an oocyte expressing ion channels of interest, a section of cell membrane, an ion channel in an artificial membrane, or some other material permitting electrical control and measurement of ion channel activity. The expression "test material" means a substance, e. g. a compound, that is being tested for stimulatory, inhibitory or modulatory activity on the test subject. The term "modulator" means a test material that alters the response of a test subject. The term "agonist" means a substance that stimulates a receptor. The term "antagonist" means a compound that blocks the activity of an agonist. The expression "recovery time" means a refractory period needed by the test subject after a stimulus is applied thereto so that the test subject can respond fully to the next-applied stimulus. The term "applicator" means a fluid-handling device that aspirates test materials (e. g., compounds of interest) from vessels and dispenses them into recording stations. The flowcell includes a "channel" or "chamber" into which fluid perfuses and allows for the transient application of test material to the test subject. Such a fluid may be, for example, a physiological saline solution that maintains viability of the test subject. The term "bath" refers to fluid surrounding and in contact with the test subject. The expression "perfusion bath" refers to fluid flowing continuously around the test subject with fresh fluid entering the bath and spent fluid exiting the bath at equal rates of flow. The expression "perfusion system" refers to the collection of devices providing a perfusion bath, such as the flowcell and its chambers or channels, tubing to instill fluid into the perfusion bath and remove fluid from the perfusion bath, and pumps or other sources of negative and positive pressure utilized to move fluid through the system. The expression "dead volume" means the volume contained within a fluid-handling component (e. g., tube or applicator) that is not utilized during an operation. In the case of this invention, the dead volume is the volume of a test material, e. g., a compound, that is aspirated from a storage vessel but not eventually dispensed into the recording station. Alternatively, "dead volume" can refer to a volume of fluid that is not exchanged by flow of the fluid, such as, for example, water trapped in a pocket at the edge of a stream. In this invention, the alternative meaning of dead volume is the area of the fluid region of the recording station that is not washed quickly by the perfusion bath.

Referring to FIGS. 1–6, the apparatus 10 comprises a deck 12 to which is attached a sampling station 14. On the deck 12 are a plurality of recording stations 16, at least one reagent rack 18, voltage clamp amplifier 20, and a wash station 22. In addition, off the deck 12 are a perfusion system 24 and a control system 26 for controlling the apparatus and acquisition of data.

The deck 12 is preferably made of a corrosion resistant material, such as, for example, aluminum. The dimensions of the deck are not critical, but it is preferred that the deck be large enough to accommodate the components that are normally placed on the deck, e. g. the recording stations 16, the reagent racks 18, the voltage clamp amplifier 20, and the wash station 22. A deck that is suitable for use in this invention has the following dimensions: 2 feet×3 feet×¼ inch.

The reagent racks 18 are stands for holding reagent vessels. The reagent racks contain a plurality of slots 27 into which the reagent vessels are inserted. There is no absolute limit to the number of reagent racks 18 that can be used with this invention. A practical limit may be imposed by the quantity of storage space available in the laboratory environment. Unlike a manifold system, which is limited by the number of compounds that can be practically tested at any one time, the availability of a plurality of reagent racks 18 greatly expands the number of compounds that can be tested during a given time period. A typical reagent rack 18 can hold from about 14 reagent vessels to about 100 reagent vessels in the slots thereof. Reagent racks 18 are commercially available and are preferably made from metal or plastic. Dimensions of reagent racks 18 suitable for this invention are not critical. The dimensions of a given reagent rack 18 are determined by the number of reagent vessels to be carried by the reagent rack. Reagent vessels suitable for use in this invention are preferably made of glass or plastic material. The reagent vessels are of a size that they conveniently fit into the slots 27 in the reagent rack 18.

Figure 8A:
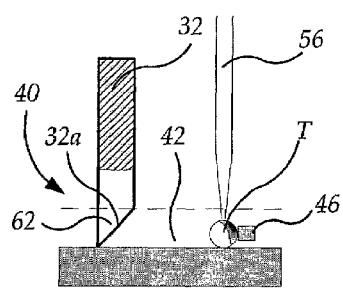
FIGS. 8A, 8B, and 8C are schematic views illustrating a sequence of steps showing the effect of a shape and a position of an applicator upon the dispensing of a test material.
Figure 8B:
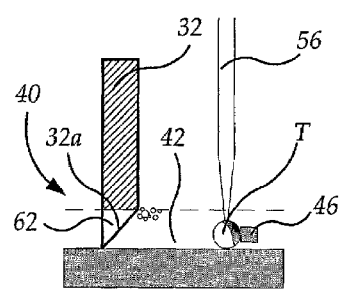
Figure 8C:
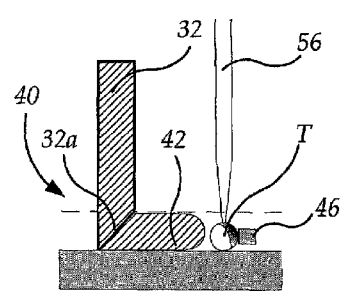

The sampling station 14 comprises an applicator 32, which is attached to an arm 34. In a preferred embodiment, the applicator 32 is substantially cylindrical in shape. The applicator 32 is connected by tubing to a pump, such as for example, a syringe pump associated with the sampling station 14. References to aspirating or dispensing by an applicator should be understood to be an action of the pump through the tubing and the applicator. The size and material of the tubing are not critical, except that the tubing and applicator 32 together should be of sufficient volume to contain and transfer the amount of fluid required in the appropriate step of the method, and that the tubing should be sufficiently long and flexible to allow requisite movement of the applicator 32. In a typical example, the length of the applicator 32 is approximately 8 to 9 inches and the diameter of the applicator 32 is approximately 0.005 to 0.010 inch. The dimensions of the applicator 32 are selected so that it can be physically accommodated within the boundaries of the apparatus, and it can provide the flow rates required in the operation. The dimensions of the applicator 32 can easily be specified by one of ordinary skill in the art. The applicator 32 from which test material, typically in the form of liquid, is delivered preferably has a beveled end 32*a* to aid in directing fluid to the test subject while allowing the escape of air from the gaps used to separate liquid solutions within the applicator 32. See FIGS. 8A, 8B, and 8C and the detailed description thereof below. Preferably, the applicator 32 is made of a rigid material that resists carryover of test material, or the applicator is coated with a material that resists carryover of test material. In a preferred embodiment, the applicator 32 is made of stainless steel and has a coating made of a low surface energy material, such as, for example, polytetrafluoroethylene. The applicator 32 is preferably attached to the arm 34 by means of a press-fit, wherein the applicator 32 is inserted through an opening in the arm 34. The arm 34 is commercially available, typically as a component of a commercially available sampling station. Movement of the arm 34 is directed by the control system 26. The arm 34 should be capable of moving in any direction required by the arrangement of the apparatus. Test materials, e. g. chemical compounds in solution, are typically drawn from an appropriate reagent vessel 36 held in a reagent rack 18, which may contain a plurality of reagent vessels. It is preferred to have a large number of reagent vessels to allow for a great variety of test materials and wide range of concentrations of test materials. It is preferred that the test materials be dispensed with a minimum level of waste and carryover. A sampling station 14 can be designed to facilitate the drawing of test materials from vessels 36 and the dispensing of test materials to the recording stations 16.

In a preferred embodiment of this invention, the sampling station 14 can be constructed from a Gilson 215 Liquid Handler modified to accommodate a wash station 22 of a size appropriate for the applicator 32, the required number of recording stations 16, and an adequate supply of reagent racks 18. The wash station 22 is included for the purpose of cleaning the applicator 32. The wash station is preferably in the shape of a well, the well having a depth and a diameter sufficient to accommodate the applicator 32. Solvents such as water and ethanol are typically used in this invention as cleaning agents, but other materials can be used. Typical durations for cleaning the applicator 32 in the wash station 22 range from about 1 to about 5 seconds.

In one embodiment of this invention, the recording station 16 comprises a flowcell 40 having a channel 42 formed therein. At one end of the channel 42 is an inlet 44 for the fluid of a perfusion bath. In the channel 42 is a barrier 46. The channel also contains a liquid level controller 48 and a vacuum pickup 50. Located in proximity to the flowcell 40 are a voltage headstage 52 and a current headstage 54. The test subject, typically a cell, such as, for example, a *Xenopus* oocyte, is represented by the letter "T". Each recording station 16 requires a set of electrodes 56. The electrodes 56 require a set of electrode manipulators 58 for positioning the electrodes near or within the test subject. The electrodes also require means for holding the electrodes in position. Such electrode holding means are known to one of ordinary skill in the art.

The flowcell 40 is preferably made of an inert material, such as, for example, polycarbonate. It is preferred that the material be inert so that it does not interact with the test subject or the test material. In a preferred embodiment, the flowcell 40 is in the shape of a block having rectangular faces. The dimensions of the block are not critical; however, a block suitable for use in this invention has the following dimensions: 3 inches×1 inch×½ inch. A channel 42 is formed in the flowcell 40. The channel 42 is open to the ambient atmosphere. The shape of the channel 42 is preferably rectangular. The channel 42 preferably has a size sufficient to accommodate the test subject. Fluid for maintaining viability of the test subject and washing out test material can enter the flowcell 40 through the inlet 44 located on the exterior of the flowcell 40. The inlet 44 connects to the channel 42 via an enclosed conduit 60. The channel 42 includes a liquid level controller 48 to regulate the level of liquid in the channel 42. The liquid level controller 48 comprises a vacuum pickup 50, to which is attached tubing (not shown) that runs to a source of vacuum (not shown). Vacuum is used to aspirate the previously instilled fluid of the perfusion bath. Located behind the test subject T is a barrier 46 for holding the test subject in place. The barrier 46 is preferably made of an inert material, so that it does not interact with the test subject or the test material. The barrier 46 should be of such a structure, dimension, and position to hold the test subject in place. Because of limited space available for the apparatus, both conventional and custom components are needed for the flowcells 40. Flowcells 40 that contain a minimum of dead volume and that feature a liquid level regulator are preferred. In a preferred embodiment, each recording station 16 includes a voltage headstage 52 and a current headstage 54. The purpose of the voltage headstage 52 and the purpose of the current headstage 54 are to measure the electrical environment and/or adjust the electrical environment of the test subject. Headstages are commercially available from Axon Instruments (Foster City, Calif.) or other electrophysiology equipment manufacturers and suppliers.

In the apparatus of this invention, a combination of commercially available manipulators 58 integrated with custom fittings can be used to carry out the required manipulation of electrodes. The manipulators 58 are selected to combine the requisite needs of compactness, precision, low drift in positioning, ease of use, and low cost, which needs are dictated by the test subject T and the electrodes 56. When *Xenopus* oocytes are the test subject, suitable electrode manipulators 58 can be constructed from inexpensive, compact micromanipulators and adapters appropriate for the dimensions of the electrodes 56 selected. Micromanipulators are commercially available from Newport Corp, (Irvine, Calif.) and Edmund Scientific (Barrington, N.J.).

The most direct approach for introducing a test material, e. g. a chemical compound, into the recording station 16 would involve the steps of aspirating the test material from a reagent vessel 36 and introducing the aspirated test material to the channel 42 of the flowcell 40. However, in the preferred embodiment, care must be taken so that the test subject in the channel 42 is not exposed to the test material before the intended time of application. In addition, in the preferred embodiment, the applicator 32 should be in contact with the fluid in the channel 42 prior to commencing application of the test material in order to minimize mechanical disturbance of the perfusion bath. Essentially, test material at the end 32a of the applicator 32, both in the interior of the applicator 32 and on the exterior surface of the applicator 32, will spread throughout the channel 42 in the flowcell 40 once the applicator 32 touches the fluid in the channel 42 (see FIGS. 7A, 7B, and 7C, where the test material is represented by diagonal lines running from the upper right to the lower left). This spread of the test material would be undesirable, because the test subject T would be exposed to the test material prior to the intended time. However, this spread of the test material can be prevented by first creating a safety gap 62 at the end 32a of the applicator 32 and then washing the interior of the applicator 32 and the exterior surface of the applicator 32 prior to application of the test material (see FIGS. 7D, 7E, 7F, 7G, and 7H, where the test material is represented by diagonal lines running from the upper right to the lower left). During this washing procedure, the applicator 32 is positioned and held in the wash station 22 for an interval of time sufficient to complete the intended wash operation. During the application operation, the applicator 32 is positioned and held in the channel 42 of the flowcell 40 for an arbitrary interval of time prior to initiating the flow of test material. In this manner, accurate baseline data can be acquired before the test material is introduced into the channel 42 of the flowcell 40 and subsequently to the test subject T.

Figure 8D:
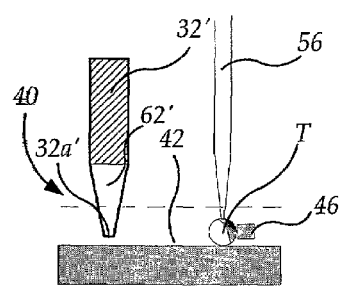
FIGS. 8D, 8E, and 8F are schematic views illustrating a sequence of steps showing the effect of a shape and a position of an applicator upon the dispensing of a test material.
Figure 8E:
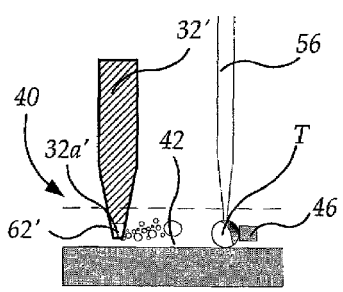
Figure 8F:
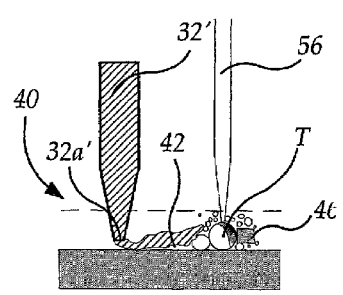

To dissipate the safety gap 62 previously described, and to provide a uniform flow front of the test material across the channel 42, the shape of the applicator 32 must be optimally selected. Certain shapes result in problems. In one straightforward design, as shown in FIGS. 8D, 8E, and 8F, an applicator 32' having a tapered end 32a' is brought into contact with the channel 42 of the flowcell 40. When the test material (represented by diagonal lines running from the upper right to the lower left) is dispensed, the air in the safety gap 62' is converted into small bubbles, which flow along the channel 42 with the test material, eventually contacting the test subject T. These bubbles can create serious measurement artifacts and can permanently damage the test subject, thereby necessitating replacement of the test subject.

Figure 8G:
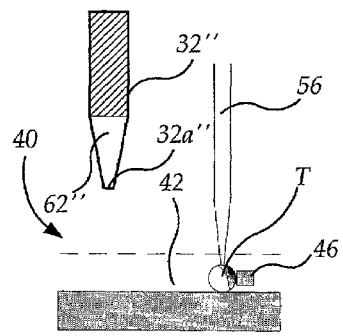
FIGS. 8G, 8H, and 8I are schematic views illustrating a sequence of steps showing the effect of a shape and a position of an applicator upon the dispensing of a test material.
Figure 8H:
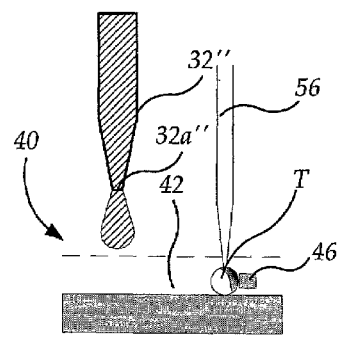
Figure 8I:
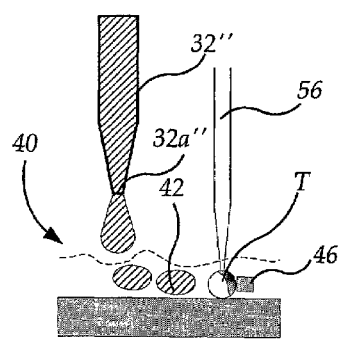

In theory, these difficulties could be alleviated by dispensing the test material in the form of a droplet stream from the end 32a" of the applicator 32" when the applicator 32" is in a position elevated above the surface of the channel 42 of the flowcell 40 (see FIGS. 8G, 8H, and 8I). This approach solves the problem of dissipation of the safety gap 62" but introduces unacceptable mechanical disturbances in the channel 42 and results in a poor initial distribution of the test material (represented by diagonal lines running from the upper right to the lower left) around the test subject T. These effects lead to artifacts and inconsistencies in the data obtained, and may even cause permanent damage to the test subject.

Amelioration of the problems associated with introducing the test material (represented by diagonal lines running from the upper right to the lower left) into the channel 42 of the flowcell 40 can be achieved by employing an applicator 32 that allows dissipation of the safety gap 62. Such an applicator 32 has a beveled end 32a that can be completely immersed in the channel 42. Such an applicator 32 will still allow the safety gap 62 to be dissipated at the surface of the channel 42, without causing bubbles to flow to the test subject T. In addition, by constructing the applicator 32 so that the end 32a is beveled and slightly smaller than the channel 42 of the flowcell 40, the applicator 32 will be self-aligned upon insertion into the channel 42, and the test material can be evenly distributed across the channel 42.

At the same time, the test subject must be sufficiently secured to prevent motion artifacts from obscuring the response to a stimulus. In the case of *Xenopus* oocytes, a small barrier 46, which can be fit into the channel 42 of the flowcell 40, can be placed on the side of the oocyte that is opposite to that of the incoming test material. This barrier 46 can be made of a variety of materials (e. g., polymeric material such as, for example, polyethylene).

A perfusion bath is supplied to maintain viability of the test subject and to wash away residual test materials or other residual substances that have been dispensed. This perfusion bath is temporarily shut off during application of the test material in order to prevent dilution of the test material. Control of the perfusion bath for each recording station 16 can be accomplished by means of a pump 72, an optically isolated relay 73 to control the pump 72, a dripper 74 to reduce pulsation, and tubing 76. The tubing 76 connects the pump 72 to the dripper 74 and the dripper 74 to the flowcell 40 of the recording station 16. The pump 72 may be a constantly operating pump equipped with a shut-off valve, or the pump 72 may be a pump capable of exhibiting intermittent pumping action. Either type of pump can be controlled by means of a computer or similar control system. A plurality of pumps, preferably one pump to serve each recording station, is located in the perfusion system 24. A plurality of peristaltic pumps (one for each recording station), preferably controlled by a computer, can be used. In FIG. 1, it should be noted that only three pumps 72, three drippers 74 and three lines of tubing 76 are shown, in order to eliminate undue complication of the figure.

To reduce pulsation artifacts caused by action of valves or by action of peristaltic pumping, and to allow an electrical break in the perfusion system, the fluid of the perfusion bath can be passed through a dripper 76. The dripper 76 is similar to the type of dripper used to deliver fluids to hospital patients intravenously. It is preferred to electrically shield the fluid of the perfusion bath along the path from the dripper 76 to the flowcell 40 in order to reduce the introduction of electromagnetic noise into the electrical recording system. Likewise, the deck 12 can be electrically grounded to act as an electromagnetic shield. In a preferred embodiment wherein *Xenopus* oocytes are used as test subjects, the pumps 72 should be able to pump fluid at a flow rate of from about 0.1 ml/min to about 5 ml/min. However, the flow rate selected may vary, depending upon the requirements of the experiment and the needs of the user. The dripper 74 in each line can be made from glass, plastic, or other suitable material. The dripper 74 in each line should contain air or other gas or fluid capable of buffering the pulsation in the flow of liquid from the pump and valve. The dripper 74 in each line should be capable of providing any requisite interruption in the electric current flow within the perfusion system. The tubing 76 connecting the pump 72 to the dripper 74 and the dripper 74 to the recording station 16 can be made from any of a variety of materials and can be of any suitable size. In the preferred embodiment, the tubing 76 should not introduce unacceptable contaminants into the fluid of the perfusion bath, should be chemically inert with respect to materials in the fluid of the perfusion bath, should be sufficiently flexible to allow for easy placement, and should have dimensions that minimize dead volume without unnecessarily restricting the flow of fluid.

A perfusion system suitable for this invention can be constructed from a set of relay closure controlled peristaltic pumps (Cole-Parmer P7720010, Vernon Hills, Ill.), optically isolated relays (Opto-22, Temecula, Calif.), inert tubing (Cole-Parmer P-95612-34, Vernon Hills, Ill.), braided shielding (Newark, Cleveland, Ohio), and a simple dripper assembly consisting of syringe barrels, rubber stoppers, and fluidic interconnections.

The need to allow for acquisition of data over a wide range of amplitudes in an automated or unattended operation necessitates operating the apparatus over a wide dynamic range. The gain needs to be sufficiently high to prevent low level signals from being lost in the quantization noise of an analog to digital (A/D) converter, but sufficiently low to prevent saturation of either the A/D converter or the voltage clamp amplifier 20. In conventional implementations, this need is met by the human user interactively adjusting the amplifier gain during the course of the experiment. This type of implementation creates difficulty in an automated system because it would require frequent attention of the user. There are three approaches for enhancing automation and reducing the need for frequent intervention by the user. One approach would be to pre-program the control software to estimate and predict the gain setting needed, based on the amplitude of each test subject's response, the anticipated behavior of the test subject to further stimulation, the anticipated effect of the next test material, and the anticipated after-effect of the previous test material. While this method is feasible, it is complicated and could introduce considerable variation according to the nature of the test subject and its response to the test material. A second approach to the problem would be to first record every response at a variety of amplifier gain settings, and then program the system to retain the data having the optimal recording, e. g., highest gain without saturation. This approach is simpler in concept than the first approach, but is more costly and complicated in that it would require additional hardware, including two or more amplifiers for every recording station and two or more sets of A/D channels per recording station. A third and even simpler solution to the problem would be to increase the resolution of the A/D converter to 16 bits (65,536 steps) from the conventional 12 bits (4,096 steps) that is characteristic of most electrophysiological systems. This modification does not require additional software programming, does not require adding hardware, and allows small responses to be resolved free from A/D artifacts while larger responses are recorded without saturation.

To obtain a measurement of the electrical properties of the test subject, such as, for example, an oocyte membrane, the electrical environment of the test subject should be controlled and monitored. In some studies, the voltage response of the test subject is measured. The voltage response can be measured in the present invention by using only the voltage headstage and the electrodes. In addition, the current headstage can be used if current-passing capabilities are also required. However, voltage-clamping is the preferred electrophysiological approach in most cases. In voltage-clamping, the test subject is held at a fixed electrical potential by an electrical current supplied thereto, and the amount of current required is measured. This voltage clamping can be accomplished by means of a voltage clamp amplifier 20. In one embodiment, the voltage clamp amplifiers 20 are controlled by commands from the control system 26 through, for example, the computer serial port and/or through a digital to analog (D/A) interface integrated into the control system 26. Voltage-clamping may be accomplished with a single headstage and electrode for each test subject, wherein this headstage and electrode assembly provides voltage-monitoring, current-passing, and current-measuring functions. Alternatively, particularly in the case of a *Xenopus* oocyte as a test subject, voltage-clamping may be accomplished through the use of two headstages and two electrodes per test subject, wherein one headstage and electrode assembly are designed for monitoring voltage, while the other headstage and electrode assembly are designed for passing current and measuring current. Voltage clamp amplifiers are commercially available and are well-known to those of ordinary skill in the art.

In the investigation of voltage-gated ion channels, it may be necessary to provide a change in the clamped potential as a stimulus. This change can be accomplished by the control software through regulation of the voltage clamp amplifier. Commonly, such commands may be issued to the voltage-clamp amplifier through the controller serial port or through the D/A converter of the control system 26.

In the present embodiment, the main purposes of this invention can be achieved by using discrete, conventional commercially available amplifiers. However, under a different set of conditions, it may become desirable to substitute customized amplifiers in order to simplify the hardware, reduce costs, reduce space requirements, or introduce custom features, such as, for example, multiple amplifiers or software-adjustable gains and filters for each recording station.

The voltage clamping component can be constructed from the following components: National Instruments Model No. PCI-MIO-16XE-50 (A/D); National Instruments Model No. AT-AO-6 (D/A); National Instruments Model No. BNC-2090 (Interface to PCI-MIO-16XE-50); and Axon Instruments GeneClamp500 Amplifier.

The control system 26 can be implemented by means of a common personal computer workstation and software created through use of standard development tools. A computer suitable for use in this invention is a Dell "Optiplex", which can run software compatible with Microsoft's Windows95 operating system. The software can be created by means of development tools commercially available from Microsoft.

In another embodiment, test subjects T can be loaded into flowcells 40 and unloaded from flowcells 40 automatically, without direct involvement of the user, so long as a method of assessing the viability of the test subject T is implemented. For example, oocytes, which serve as the test subjects, can be loaded into flowcells 40 and unloaded from flowcells 40 by using the applicator 32 of the sampling station 14 to move the oocytes and by using computer controlled motors to manipulate the electrodes 56. A sequence for loading and unloading an oocyte is illustrated in FIGS. 19A through 19E and FIGS. 20A through 20F. The applicator 32 is positioned above an oocyte contained in a vessel 80 (see FIG. 19A). The applicator 32 penetrates the meniscus (designated by the letter "M") and dispenses a sufficient amount of fluid to disturb the oocyte (see FIG. 19B), thereby freeing the oocyte from the wall of the vessel 80. The oocyte then sinks to the bottom of the vessel 80 (see FIG. 19C). Light suction is applied through the applicator 32 to capture the oocyte (see FIG. 19D), and the oocyte is removed from the vessel 80 for transporting to a flowcell 40 (see FIG. 19E).

In FIG. 20A, the electrodes 56 are shown as being retracted from the channel 42 of the flowcell 40. The applicator 32, which contains the oocyte, is then inserted into the perfusion bath of the channel 42 of the flowcell 40 (see FIG. 20B). The oocyte is then gently pushed into the perfusion bath in the channel 42 of the flowcell 40 by means of a pulse of fluid from the applicator 32 (see FIG. 20B). The channel 42 is designed in such a way that the position of the oocyte is known when it comes to rest. This design of the channel 42 can be effected in various ways, such as, for example, forming a channel having a narrow width, forming a depression in the channel, or forming guides in the channel. After a sufficient interval of time (e. g., 2 to 5 seconds), the electrodes 56 are inserted into the perfusion bath in the channel 42, and their electrical junction potentials are offset to 0 mV (see FIG. 20C). The oocyte is detected by advancing the electrodes 56 towards the bottom of the channel 42 (see FIG. 20D). If an electrode 56 successfully penetrates the oocyte, a change in electrical potential will be observed on that electrode 56. The electrodes 56 are advanced until each one registers an appropriate potential or reaches a preprogrammed length of travel (see FIG. 20D). If an oocyte is not detected or if its electrical potential is inadequate, which suggests a dead or leaky oocyte, the oocyte is removed from the flowcell 40. In FIG. 20E, the electrodes 56 are shown as being retracted. The applicator 32 is brought into contact with the oocyte, and the oocyte aspirated (see FIG. 20F). The oocyte then may be discarded or stored in an appropriate vessel. If the oocyte is detected, it is then voltage-clamped and its holding current measured. If this holding current is higher than acceptable, the oocyte may be discarded or stored in the manner previously described. If this holding current is acceptable, the oocyte is tested for a valid response to a control. If this response is not adequate, in terms as defined by the user, the oocyte is discarded. If the oocyte passes all required tests, experiments are scheduled to be performed on it. If at any time the oocyte fails to respond adequately to a control, or its holding current rises above a set point defined by the user, the oocyte is replaced. If there is a higher than expected number of failures for a given flowcell 40, that flowcell 40 is disabled until the user intervenes. This manner of automation allows the system to be run for long periods of time and to perform numerous tests without requiring substantial intervention by the user.

In the course of high throughput screening, large numbers of compounds can be applied to the test subjects. It is desirable to retest responses to a control at intervals defined by the user in order to determine whether the test subject remains responsive. If the responsiveness of the test subject declines substantially, the test subject is replaced, and further testing resumes. Such further testing typically includes retest of those applications made during the period of low responsiveness. The purpose of this procedure is to minimize false negatives.

OPERATION

The apparatus and method of this invention can be used with many types of test subjects. However, for the sake of simplification, the discussion of operation that follows will refer primarily to *Xenopus* oocytes as test subjects. Fluid handling operations vary according to the protocol chosen and will be treated in detail later. For a typical sequence of fluidic events refer now to the sampling station 14. The arm 34 moves the applicator 32 to the wash station 22 for cleaning. Then, an air safety gap 62 is formed at the end 32*a* of the applicator 32 by means of aspiration. The arm 34 then moves the applicator 32 to the appropriate vessel 36, and the applicator 32 aspirates the amount of test material specified in the experimental set-up (see FIG. 5A). After another smaller air safety gap is aspirated, the exterior surface of the applicator 32 is cleaned at the wash station 22 (see FIG. 5B). The arm 34 then moves the applicator 32 to the appropriate recording station 16 and dispenses the test material into the channel 42 of the flowcell 40 (see FIG. 5C). During the dispensing of the test material, electrophysiological data are acquired. See FIGS. 6A, 6B, and 6C, which show current measured as a function of time. FIG. 6A shows current measured as a function of time before application of the test material. FIG. 6B shows current measured as a function of time during application of the test material. FIG. 6C shows current measured as a function of time after application of the test material. After completion of the dispensing of the test material and the acquisition of data, the applicator 32 is cleaned at the wash station 22 (see FIG. 5D), loaded with a test material from another vessel (see FIG. 5A), and performs another dispensing operation for the test subject that is next on the schedule (see FIGS. 5B, 5C. and 5D). Test subjects are allowed to recover before a subsequent application of a test material thereto.

Experiments can be programmed by using the software tools of this invention. A human user selects test materials, concentrations thereof, and protocols. A run file is generated by the computer; the run file lists the experiments and the test materials. The user then loads the reagent racks 18 onto the deck 12 and activates the pumps 72 for the channels 42 of the flowcells 40 of the recording stations 16 that will be used.

When oocytes are loaded into the channels 42 of the flowcells 40 of the recording stations 16, the the cell membranes of the oocytes are penetrated with the electrodes 56 through the use of the electrode manipulators 58 and the apparatus is ordered to test the oocytes for a valid response to a control. If a given oocyte does not produce a valid response, a new oocyte can be loaded in its place and tested in the same way. Once all the oocytes are loaded, the automated protocol is started and experiments are scheduled to run on the appropriate oocytes. At any time, experiments can be reviewed, rejected, or rescheduled. A run may also be paused and oocytes unloaded from the recording station 16 or loaded onto the recording station 16 without the loss of information and without the loss of experiment control.

To coordinate the activities of sampling, dispensing, scheduling, reviewing, and collecting data, software was developed for the control system 26 to fully automate the process.

In a conventional electrophysiological experiment, the user must closely monitor the condition and responses of the test subject, making adjustments of the recording conditions and test materials to be delivered. This requirement is, of course, antithetic to the desire to have unattended operation where operations are performed in batches with little or no human intervention. At the same time, it is not efficient for experiments to be run in a purely batch-oriented mode, given the failure rate for individual electrophysiological experiments. This failure rate is frequently due to the limited life span of the test subject.

The control software described herein addresses these competing criteria by means of an Interactive-Batch Mode system. In this system, the user sets up the protocol, prepares the test material, sets the appropriate test subjects in the recording stations 16, and then allows the system to conduct the desired series of experiments in an unattended manner. At any time during the data collection process, the user may monitor the responses of the test subjects and review all the logged data. Individual data points or sets of experiments may be "flagged" as unsuitable and the experiments can be repeated on the same test subject or another. This dynamic scheduling can be performed either while the system is running or while the system is paused. This flexibility allows all the tests of an experiment to be carried out even in the event of premature failure of the test subject.

The following describes one typical interaction between a human user and the system of this invention. However, it should be understood that this interaction is merely exemplary, and is not intended to limit the scope of this invention. To begin a session, the user enters his/her name and notebook references. To construct a set of experiments, the user selects a named single protocol; however, in preferred embodiments, a plurality of protocols can be selected. The user then sets the parameters for the entire protocol(s). Such parameters may include, but are not limited to, flow rate of test material, start time of test material application, stop time of test material application, duration of introduction of test material, recovery period of test subject, name of control material, concentration of control material, control repetition interval, digital sampling rate, temperature of said test subject, and electrophysiological holding potential. These parameters can be stored and recalled later so that the user can create any number of files specifying routine sets of parameters, i. e., many parameters can be specified by one simple name.

After the parameters for this session are selected, the user selects which test materials will be tested along with which test subject types the test materials will be tested against. For example, test material "A" could be tested on test subject types "VR-1" and "VR-2", while test materials "B" and "C" would be tested only on test subject type "P2X". These experiments can be run concurrently without fear of interference among each other. For each compound, a set of doses is specified (e. g., 1 nM, 3 nM, 10 nM, 30 nM, 100 nM, 300 nM) and the number of replicates entered. The user can also specify how many of these identical experiments are performed upon distinct test subjects.

After defining the types of experiments and the number thereof, the user decides what type(s) of reagent rack(s) 18 is/are appropriate (types of reagent racks may be mixed on the deck as needed). The software analyzes the foregoing selection(s) and decides whether the selection(s) is/are tenable. If tenable, the software selects the locations of all reagents needed along with the quantities and concentrations thereof. This list can be either printed or exported for solutions to be made at a separate sampling station.

The deck position parameters are then selected. For each recording station 16 (e. g., recording stations 1 through 6, inclusive), a test subject type, clamp voltage, perfusion bath type, and flow rate are selected.

Figure 13:
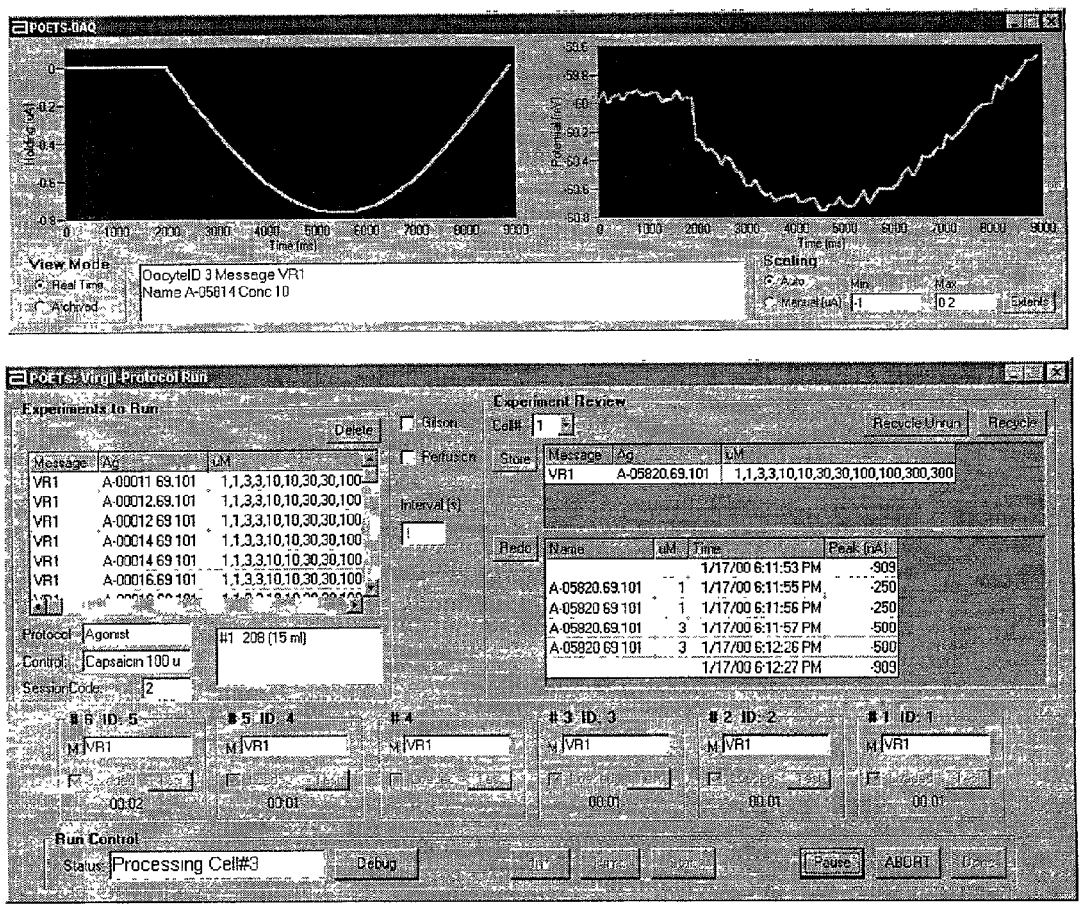
FIG. 13 is a screenshot of a graphical user interface for the control system of the apparatus of this invention.

FIG. 13 shows a typical sample of a run screen during data acquisition. This run screen depicts a hypothetical run. The individual test subject positions can be selected and the data collected thus far previewed. Individual responses, as well as entire experiments, may be rejected and rescheduled. Test subjects may be loaded into the recording stations 16 on the deck 12 and unloaded from the recording stations 16 on the deck 12. As the responses are collected, they are logged into the database.

Experimental protocols will now be described. In the agonist protocol, the test material is tested over a range of concentrations specified by the user for activity that mimics that of a known endogenous or exogenous agonist. In order to compare results over the course of a series of experiments on the same or a different test subject, a known reference agonist is dispensed and its response recorded. This procedure allows normalization to this known reference agonist during the data analysis phase.

In the modulator (or antagonist) protocol, the experiments are designed to determine how the test material alters the response of the test subject to a known agonist. The basic procedural steps are similar to those of the agonist protocol, but there are two distinct dispensing steps. The first step involves dispensing only the modulator (or antagonist) at a specific concentration; data may be recorded at this stage if desired. In this step, the test subject is pre-exposed to the test material. Accordingly, no cleaning of the exterior surface of the applicator is required. In the next dispensing step, the test material and the known agonist are dispensed together. The response of the test subject to this combination is recorded, along with the baseline and recovery data.

A voltage-gated protocol is similar to the modulator protocol in that it evaluates the effect of the test material on the response to a known stimulus. Instead of a ligand stimulus (agonist), an electrical stimulus is used. First, baseline data is collected (data from an electrical pulse/ramp train specified in the protocol), and then the test material is applied, followed by a repeat of the electrical stimulus previously applied.

Figure 9:
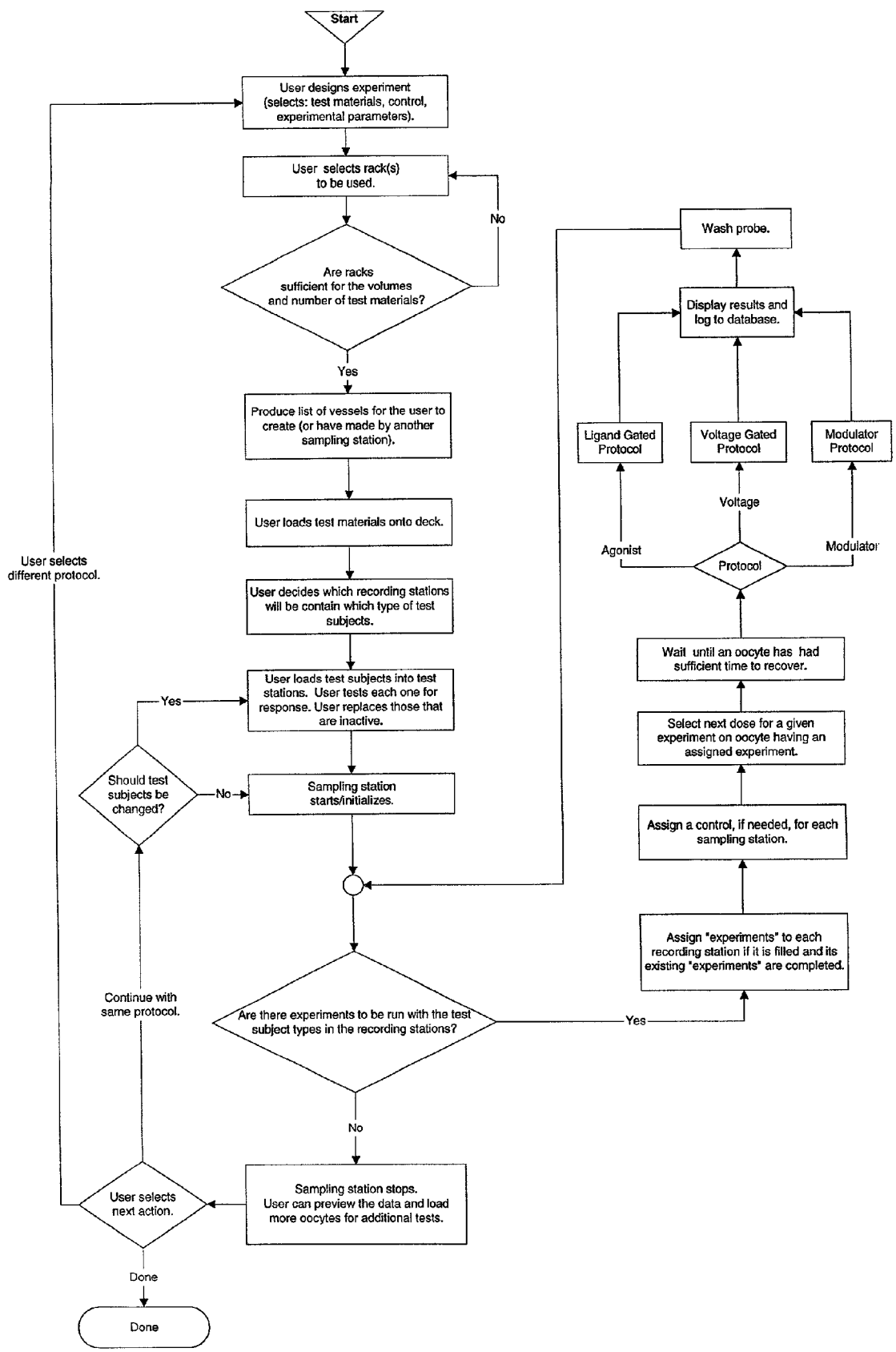
FIG. 9 is a flowchart depicting the overall operation of the apparatus and method of this invention.
Figure 10:
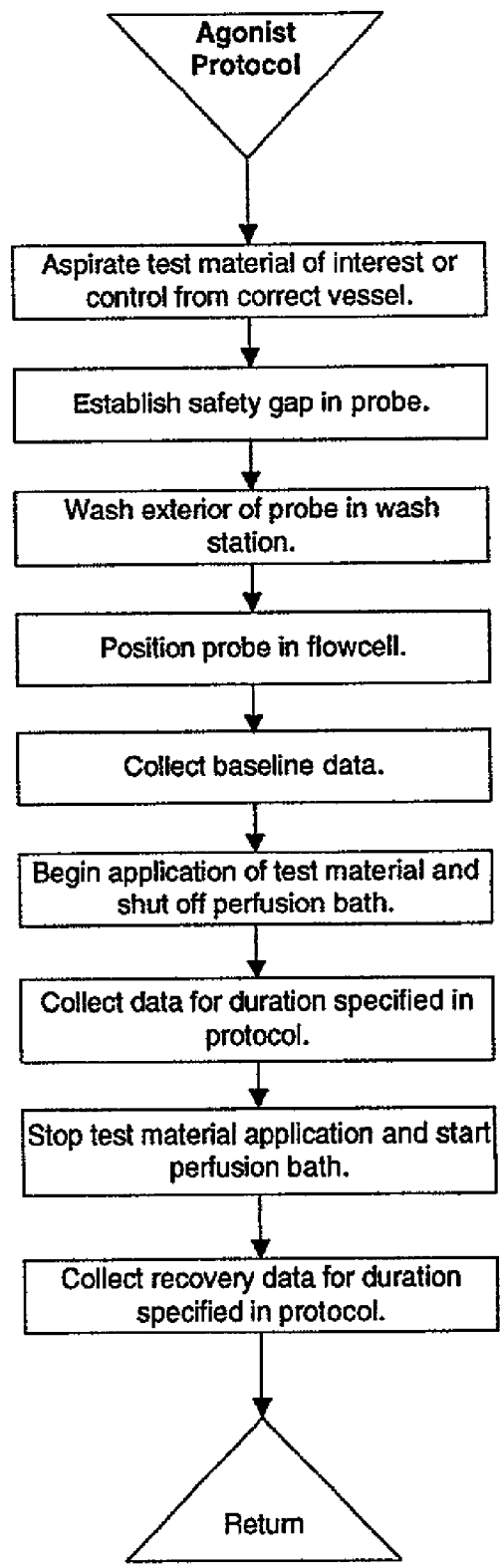
FIG. 10 is a flowchart depicting the operation of the agonist protocol of the method of this invention.

FIGS. 9, 10, 11, and 12 illustrate in detail how protocols of the present invention can be planned and executed. In these illustrations, and in FIG. 14, human activities are prefaced by the term "User." Activities carried out by the apparatus do not state the term "User." FIG. 9 is a flowchart that illustrates the overall capabilities of the method of this invention. As a first step, the experiment is designed (i. e., a selection of test materials, experimental parameters, and control test material is made). Then the reagent rack(s) 18 to be used are selected. If the reagent rack(s) 18 selected are not sufficient for the number and required volumes of the test materials, additional reagent rack(s) are selected by user. When it is determined that the reagent rack(s) 18 selected are sufficient for the number and volumes of the test materials, a list of test materials and their locations is displayed for the user to create solutions of test materials. Reagent rack(s) 18 containing these test materials are then loaded onto the deck 12 by the user. The user decides which recording stations 16 will be populated with which test subject types. The user loads test subjects into the recording stations 16 on the deck 12 and tests each test subject for a response. The test subjects that are inactive are replaced. Alternatively, test subjects may be loaded or unloaded and tested by means of automated components, such as, in the case of oocytes, automated applicators and automated electrode manipulators. At this point, the sampling station protocol commences. The sampling station 14 primes itself if needed by pumping fluid through the applicator 32 into the wash station 22. The control system 26 determines whether there are experiments to be run with the types of test subjects in the recording stations 16 on the deck 12. If there are no experiments to be run, the sampling station 14 stops. If there are additional experiments to be run with the types of test subjects in the recording stations 16 on the deck 12, the control system 26 assigns experiments to each recording station 16 on the deck 12; if an assigned recording station 16 is filled, the control system 26 insures that it has at least one incomplete experiment assigned (if there are experiments left to run). The control system 26 then selects the next concentration of test material for the current experiment for each test subject loaded. The control system 26 then determines whether a control needs to be run. This preempts the current experiment. The apparatus waits until one of the test subjects has had sufficient time to recover. At this stage, steps unique to the specific protocol occur. These steps are detailed in detail later. Data resulting from these steps is logged to the database and then displayed. The applicator 32 is then washed and the process starts on the next available test subject.

Specific protocol dependent steps follow. If the protocol calls for an agonist, the procedure is as follows (see FIG. 10). The test material, e. g., compound of interest or control, is aspirated from the correct reagent vessel. A safety gap is formed in the applicator 32. The exterior surface of the applicator 32 is washed. The applicator 32 is placed into proper position with respect to the channel 42 of the flowcell 40 of the recording station 16. Baseline data is collected. Then the test material is dispensed into the channel 42 of the flowcell 40 of the recording station 16, while the perfusion bath is shut off to prevent dilution of the test material during its application. Data on membrane current are collected for the duration specified in the protocol as the test material is dispensed. The perfusion bath is started after all the test material is dispensed. Data collection continues for the duration specified by the user.

Figure 11:
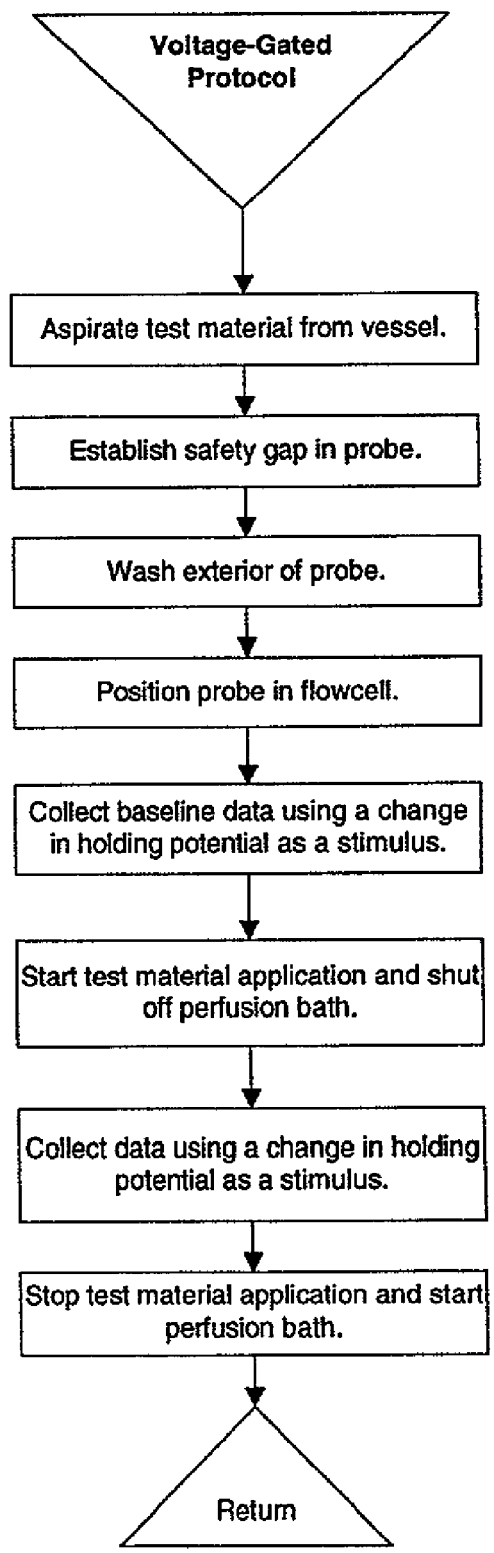
FIG. 11 is a flowchart depicting the operation of the voltage stimulus protocol of the method of this invention.

If the protocol calls for stimulation in the form of a time-variant electrical potential, the procedure is as follows (see FIG. 11). The test material is aspirated from the correct reagent vessel. A safety gap is established in the applicator 32. The exterior surface of the applicator 32 is washed at the wash station 22. The applicator 32 is placed into proper position with respect to the channel 42 of the flowcell 40 of the recording station 16. Baseline data is collected. Then the test material is dispensed into the channel 42 of the flowcell 40 of the recording station 16, while the perfusion bath is shut off. Data are collected for the duration specified in the protocol. The application is completed and the perfusion bath is started.

Figure 12:
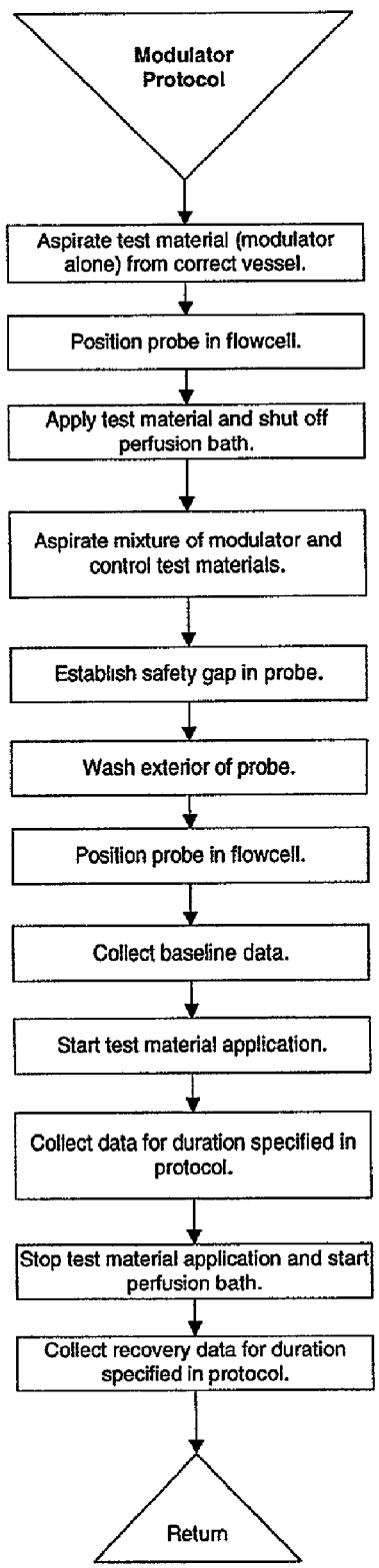
FIG. 12 is a flowchart depicting the operation of the modulator protocol of the method of this invention.

If the protocol calls for a modulator or antagonist (see FIG. 12), the test material is aspirated from the correct reagent vessel. The applicator 32 is placed into proper position with respect to the channel 42 in the flowcell 40 in the recording station 16. The perfusion bath is shut off and the modulator or antagonist is applied; data may be collected at this stage if desired. The modulator or antagonist plus control test material is aspirated. A safety gap is formed in the applicator 32. The exterior surface of the applicator 32 is washed at the wash station 22. The applicator 32 is placed into proper position with respect to the channel 42 in the flowcell 40 of the recording station 16. Baseline data is collected. Then the test material is dispensed into the channel 42 of the flowcell 40 of the recording station 16, while the perfusion bath is shut off. Data is collected for the duration specified in the protocol as the test material is dispensed. The perfusion bath is started after all the test material is dispensed. Data collection continues for the duration specified by the user. FIGS. 9 and 12 indicate the modulator protocol only. The antagonist protocol would involve replacing the term "modulator" with the term "antagonist" in FIGS. 9 and 12.

Figure 14:
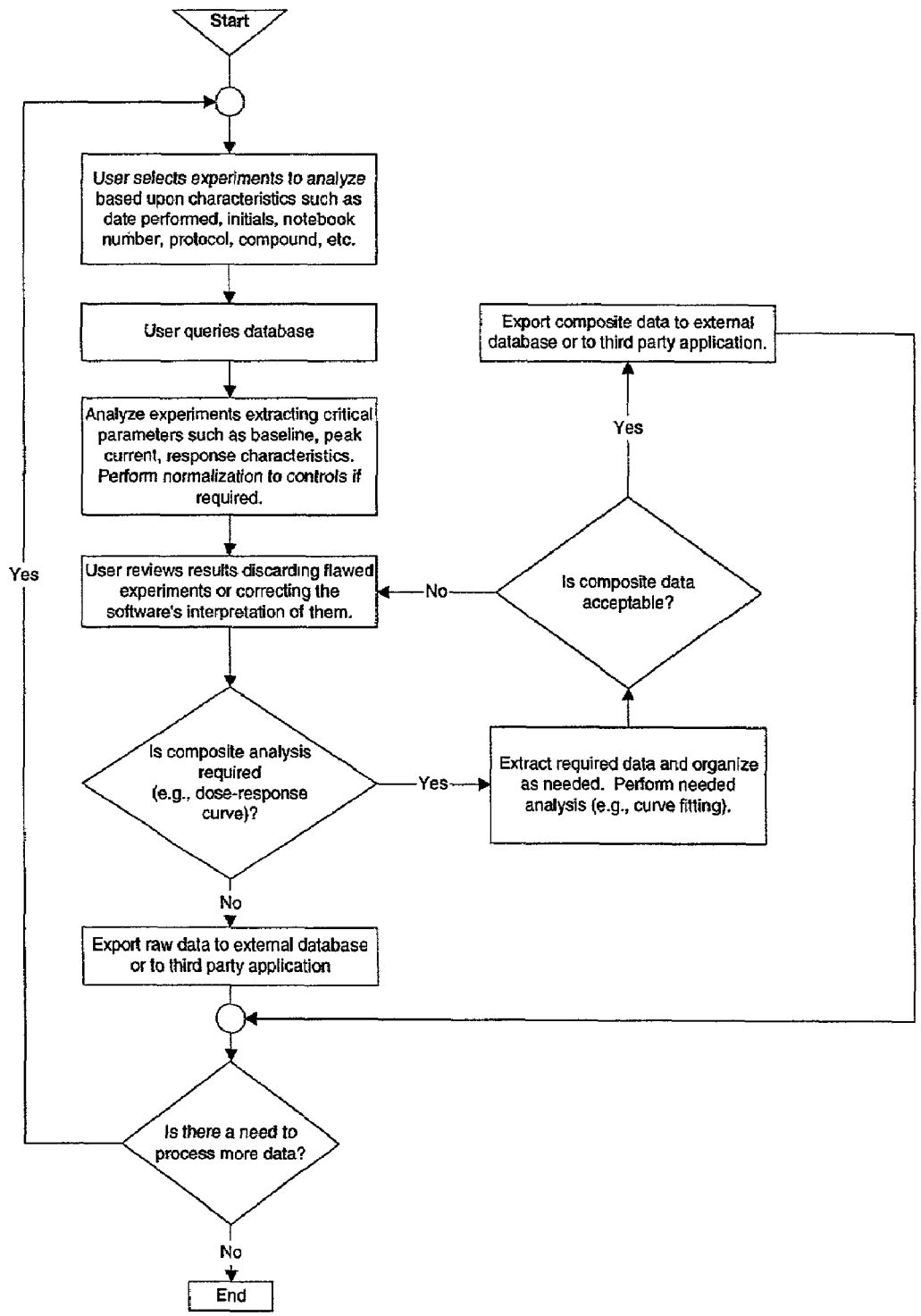
FIG. 14 is a flowchart depicting the operation of the data analysis software of this invention.

FIG. 14 is a flowchart that illustrates the data analysis of the method of this invention. This software provides an integrated framework with which to organize and perform the data analysis needed in order to interpret the experimental results. The user selects experiments to analyze, based upon characteristics such as date performed, initials, notebook number, protocol, test material, and the like. The user then queries the experimental database. The software then analyzes the experiments by extracting critical parameters, such as baseline, peak current, wave form characteristics. The software also performs normalization to controls, if required. The user reviews the results, discarding experiments deemed to be in error (e. g., due to a failure in the recording fidelity) or modifying the software's interpretation of the response (e. g., correcting automated peak detection). If a composite analysis is not required, the raw data is exported to an external database or to a separate application. If there is no need to process more data, the program comes to an end. If there is a need to process more data, the program returns to the selection step. If a composite analysis is required, the software extracts the required data and organizes it as needed. The software then performs the analysis required. An example of such an analysis is curve fitting. If the composite analysis is not acceptable, the user reviews the results, discarding experiments or correcting the software's interpretation of them. If the composite data is acceptable, the composite data is exported to an external database or to a separate application. The program then returns to the question of the need to process more data.

Thus, the software of this invention integrates data extraction and analysis functions that conventionally would be performed across several separate programs. These separate programs require tedious manual operations to transfer data from one program to another. The software of this invention reduces error and reduces the time required for analysis of data by more than an order of magnitude.

The method and apparatus of this invention can be used with other test subjects and other test materials. Other test subjects include, but are not limited to, other types of cells, tissue (e. g., muscle), and noncellular entities (organic or nonorganic). Other test materials, in addition to electrical measurements, include, but are not limited to, mechanical measurements (e. g., muscle contraction) and optical measurements (e. g., of a fluorescence dye or an absorbance dye used as a probe, or of light output as a direct response). Furthermore, the method and apparatus of this invention are amenable to many types of stimuli. These stimuli include, but are not limited to, chemicals, mechanical forces, light, temperature, and any other stimuli to which the test subjects respond in a quantifiable manner. Examples of chemical stimuli include receptor or channel agonists, antagonists, and modulators. Examples of mechanical force stimuli include muscle tension and membrane displacement for mechanoceptors. An example of a light stimulus includes retinal phototransduction. Examples of temperature stimuli include hot and cold nociceptors.

The following non-limiting examples further illustrate the invention.

EXAMPLES

Comparative Example A (Prior Art)

This example illustrates the time and material required by a conventional system to determine concentration-response curves (six concentrations for each curve—3 nM, 10 nM, 30 nM, 100 nM, 300 nM, and 1 μM) for ten test materials (such as receptor agonists) at three different receptor types expressed in *Xenopus* oocytes. Typically, each compound at each concentration is to be tested in duplicate, and each curve is to be derived from at least two oocytes expressing the same receptor subtype. Controls (reference agonist at one set concentration) are to be tested in duplicate at the beginning, middle, and end of each set of concentrations for a given test material. Thus, there will be a total of 18 applications of test material or reference agonist per concentration-response curve. Each application of material extends for a period of 10 seconds at a flow rate of 3 ml/min. After each agonist application, a 3-minute rest/washout interval is imposed to allow for the receptor refractory period.

The conventional manifold system comprises eight lines, six to test agonist at different concentrations, one for reference agonist, and one for wash. The manifold system also comprises a single outlet. The volume of tubing, valves, and manifold between the reservoir containing the agonist and the test oocyte is 2 ml. The oocyte system is a single oocyte system, i. e., data are recorded from one oocyte at a time in one recording station with one eight-line manifold applying compounds to the oocyte.

The time required to complete one concentration-response curve for one compound at one oocyte is 51.1 minutes plus set-up time (i. e., the time required to install the test subject, make and install appropriate test material and perfusion solutions, and establish electrophysiological recording). The time required to complete two concentration-response curves (one compound, one receptor subtype, each of two oocytes) is 105.1 minutes plus set-up time. The time required to complete six concentration-response curves (one compound, three receptors in duplicate) is 321.1 minutes plus set-up time. The time required to complete all the concentration-response curves for ten compounds is 3237 minutes (54 hours) plus set-up time. Thus, at least one full working day would be required to test only one compound in duplicate at all three receptors. Ten full working days would be required to test all ten compounds in duplicate at all three receptors. This work actually would be spread over a 2½-week period because such recording typically would be done only four days per week; the fifth day of the work-week is required for test subject preparation and data review.

The amount of each test material used is at least 12 nanomoles, ignoring material loss to weighing and solution transfer, and assuming that 8 ml solution is sufficient for each concentration of test material, that the tests for each compound are completed in one day, and that test material solutions can be stored overnight.

Example 1

The purpose of this example is to illustrate the time and material required by the present invention to perform the same measurements described in Comparative Example A. Six oocytes are mounted in six recording stations 16 on the deck 12 at one time. The oocytes represent three receptor subtypes in duplicate. Ten compounds in six concentrations each (60 vessels plus one vessel for reference compound) are mounted on the deck.

The time required perform one concentration-response curve for one compound at one oocyte is 51.1 minutes plus set-up time. The time required to run two concentration-response curves for one compound (one receptor subtype, each of two oocytes) is 51.5 minutes plus set-up time. The time required to run ten concentration-response curves for one compound at each of three receptors in duplicate is 53.5 minutes plus set-up time. The time required to run all concentration-response curves for all ten compounds is 540 minutes plus set-up time. Thus, the measurements that required a full 2½ weeks to perform using the conventional instrument could be done within two working days using the present invention.

A minimum of 10 nanomoles of each test material is required, ignoring material loss to weighing and solution loss to pipettes and vessels.

Comparative Example B (Prior Art)

This example illustrates the time and material required by a conventional system to determine concentration-response curves for ten antagonists or modulators, with dosage, replication and reference agonist requirements similar to those indicated in Comparative Example A. Antagonists and modulators need to be introduced into the perfusion bath containing the test subject for equilibration prior to applying test agonist in the presence of antagonist or modulator.

In contrast to the agonist example (Comparative Example A), the time requirements for testing antagonists or modulators would increase by about 35 minutes for each compound, assuming that the compound washes out of the system quickly (within 15 minutes).

Material usage would be about 145 nanomoles per compound, assuming all tests for each compound are completed in one day or that the saline solutions are stable in storage until the next experiment. Usage of compound in antagonist testing is higher than for agonist testing, because the test material needs to be perfused into the bath and the test subject needs to be equilibrated with the test material prior to testing the effect of the test material on the response to the reference agonist.

Alternatively, the manifold system can be used to apply the antagonist or modulator before the reference agonist is applied in the presence of the antagonist or modulator. This alternative dramatically decreases material usage, but dramatically increases the time required, because now only half as many concentrations can be tested per each manifold set-up. Two lines are required for each concentration of the antagonist or modulator—one for the antagonist or modulator alone and one for the reference agonist in the presence of the antagonist or modulator. Thus, in an 8-line manifold, only four concentrations of one test material could be tested in a given set-up.

Example 2

To perform the antagonist or modulator measurements described in Comparative Example B, the present invention would require only slightly more time than it required to run the agonist experiments described in Example 1. However, the present invention would use relatively little material—19 nanomoles of each test material—while maintaining the capacity to run many different test materials and test subjects, important factors that are lost in the conventional manifold system considered above.

Example 3

Figure 15:
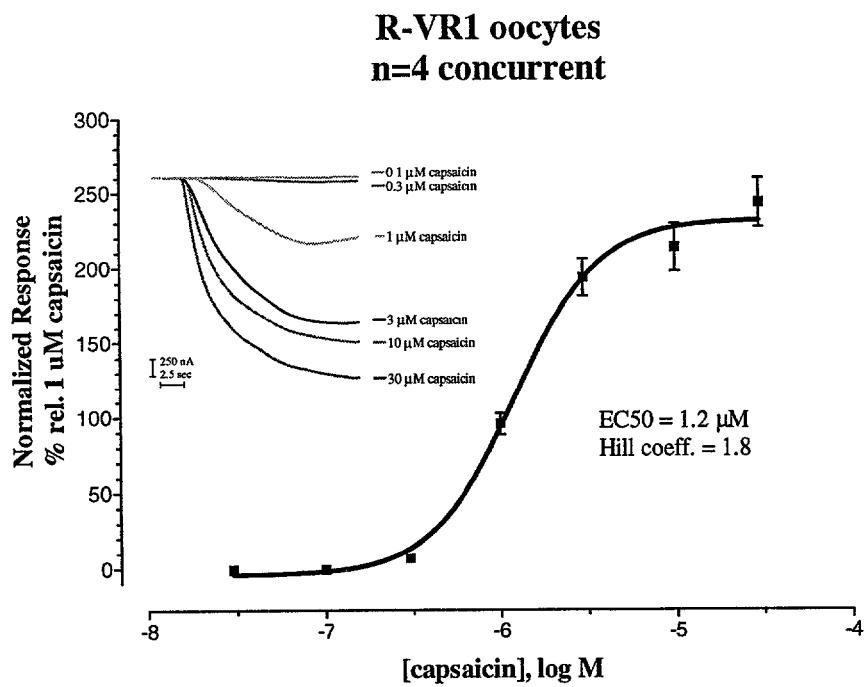
FIG. 15 is a graph illustrating the normalized response of *Xenopus* oocytes to an agonist as a function of the logarithm of the concentration of an agonist.

FIG. 15 shows the normalized response to an agonist as a function of its logarithm of concentration for four $Xenopus$ oocytes exogenously expressing a type of rat vanilloid receptor abbreviated R-VR1. The four oocytes were tested concurrently in the apparatus of this invention. Each oocyte was exposed to the agonist capsaicin at various concentrations ranging from 0.03 $\mu$M to 30 $\mu$M. In each oocyte, responses were referenced (normalized) to control responses (1 $\mu$M capsaicin) in order to correct for the degree of receptor expression and sensitivity. The data points in the graph show the normalized responses from all four oocytes as mean±standard error of the mean, and the curve represents the Hill equation fitted to these data points. The inset shows a family of responses recorded from one of the four oocytes; individual responses to various concentrations of capsaicin are overlaid.

Example 4

Figure 16:
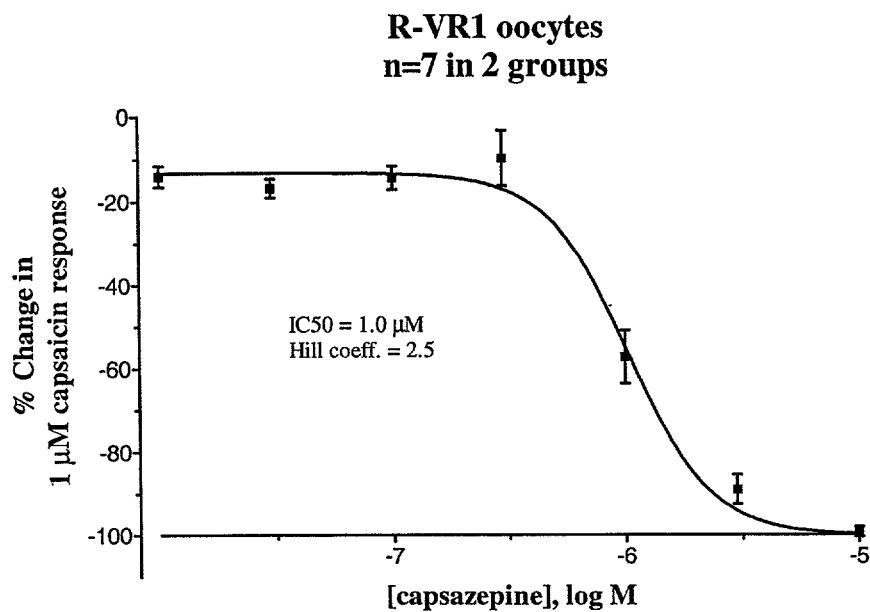
FIG. 16 is a graph illustrating the percentage change in response of *Xenopus* oocytes to an agonist as a function of the logarithm of the concentration of a modulator.

FIG. 16 shows the percentage change in R-VR1 response as a function of the logarithm of antagonist concentration. Data are from seven $Xenopus$ oocytes exogenously expressing R-VR1, tested in two groups in the apparatus of this invention. In each group, a plurality of oocytes was tested concurrently in the apparatus of this invention. These experiments evaluated the ability of the antagonist capsazepine, in concentrations ranging from 0.01 $\mu$M to 10 $\mu$M, to inhibit the response to the agonist capsaicin (1 $\mu$M). The data points in the graph show the change in the capsaicin response amplitude as a function of the concentration of capsazepine as mean±standard error of the mean, and the curve represents the Hill equation fitted to these data points.

Example 5

Figure 17:
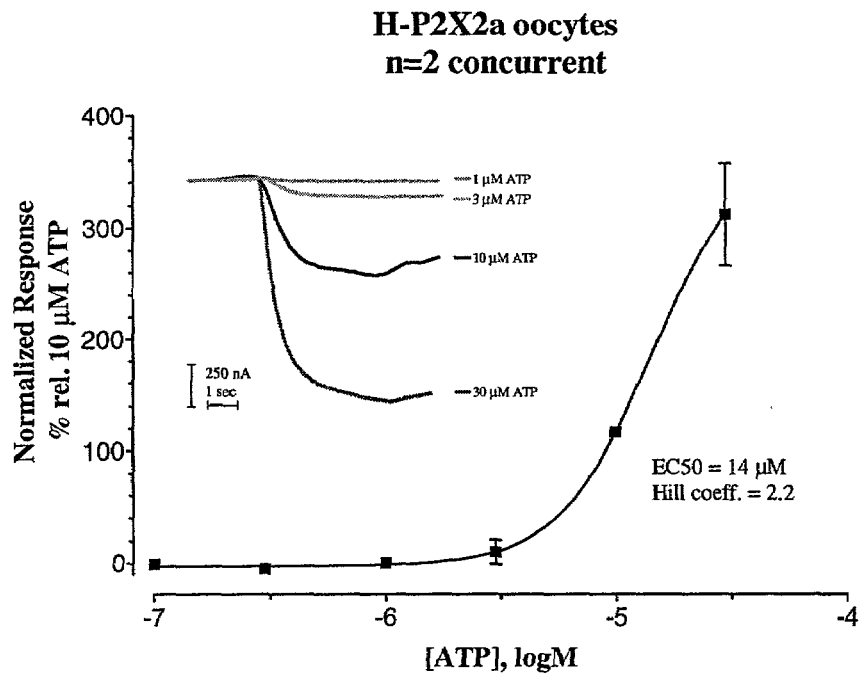
FIG. 17 is a graph illustrating the normalized response of *Xenopus* oocytes to an agonist as a function of the logarithm of the concentration of an agonist.

FIG. 17 shows the normalized response to an agonist as a function of its logarithm of concentration for two $Xenopus$ oocytes exogenously expressing the human purinergic receptor P2X2a (H-P2X2a). The two oocytes were tested concurrently in the apparatus of this invention. Each oocyte was exposed to the agonist ATP at various concentrations ranging from 0.1 $\mu$M to 30 $\mu$M. In each oocyte, responses were referenced to the control (10 $\mu$M ATP) response in order to correct for the degree of receptor expression and sensitivity. The data points in the graph show the normalized responses from the two oocytes as mean±standard error of the mean, and the curve represents the Hill equation fitted to these data points. The inset shows a family of responses recorded from one of the oocytes; individual responses to various concentrations of ATP are overlaid.

Example 6

Figure 18:
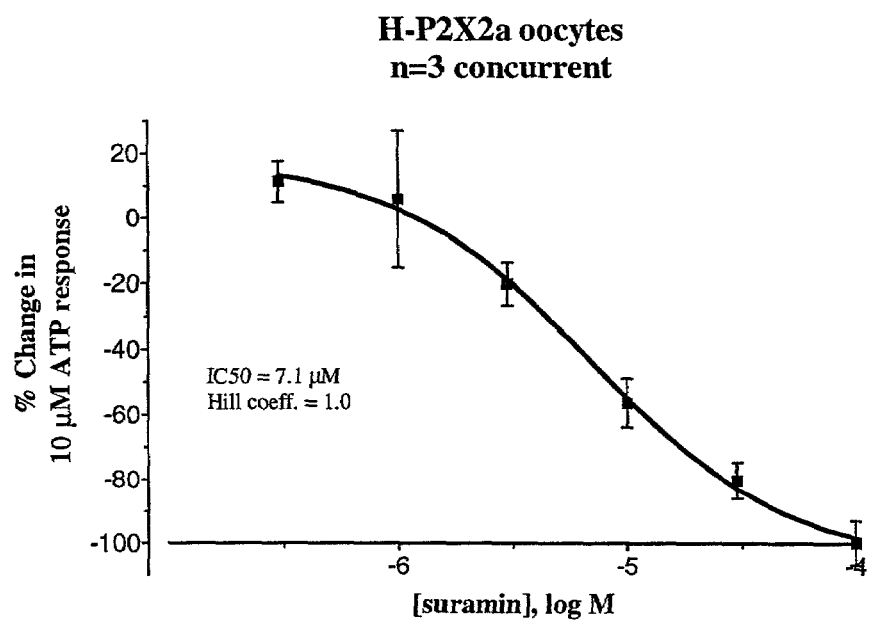
FIG. 18 is a graph illustrating the percentage change in response of *Xenopus* oocytes to an agonist as a function of the logarithm of the concentration of a modulator.

FIG. 18 shows the percentage change in H-P2X2a response as a function of the log of antagonist concentration. Data are from three *Xenopus* oocytes exogenously expressing H-P2X2a receptors. The oocytes were tested concurrently in the apparatus of this invention. These experiments evaluated the ability of the antagonist suramin, in concentrations ranging from 0.3 $\mu$M to 100 $\mu$M, to inhibit the response to the agonist ATP (10 $\mu$M). The data points in the graph show the change in the capsaicin response amplitude as a function of the concentration of capsazepine as mean±standard error of the mean, and the curve represents the Hill equation fitted to these data points.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A method for running a plurality of tests to obtain electrophysiological data, the method comprising the steps of:
   (a) providing a plurality of recording stations, each of said recording stations capable of containing at least one test subject;
   (b) introducing at least one test subject into a first one of said plurality of recording stations;
   (c) introducing at least one test subject into a second one of said plurality of recording stations;
   (d) assessing the viability of said at least one test subject in said first one of said plurality of recording stations;
   (e) assessing the viability of said at least one test subject in said second one of said plurality of recording stations;
   (f) introducing at least one test material into at least one of said plurality of recording stations that contains a viable test subject as determined by the assessment made in steps (d) and (e), wherein a movable applicator introduces said at least one test material of step (f) directly into at least one of said plurality of recording stations;
   (g) replacing said at least one test subject in said first one of said plurality of recording stations if said at least one test subject in said first one of said plurality of recording stations fails to respond adequately to a control or if the electrophysiological data of said at least one test subject in said first one of said plurality of recording stations exceeds a user-defined set point;
   (h) replacing said at least one test subject in said second one of said plurality of recording stations if said at least one test subject in said second one of said plurality of recording stations fails to respond adequately to a control or if the electrophysiological data of said at least one test subject in said second one of said plurality of recording stations exceeds a user-defined set point; and
   (i) collecting said electrophysiological data from each of said plurality of tests, wherein the steps (b), (c), (d), (e), (f), (g), (h), and (i) are carried out without substantial intervention by a human operator, further including the step of disabling said first one of said recording stations if said first one of said recording stations has a higher than expected number of failures, the expected number of failures being defined by the user.

2. The method of claim 1, wherein each of said recording stations comprises:
   (a) a holder for said test subject;
   (b) a means for measuring the electrical response of said test subject to said at least one test material.

3. The method of claim 2, wherein each of said recording stations further includes a controller for controlling the electrical environment of said test subject.

4. The method of claim 1, wherein said at least one test material is introduced by means of a fluid stream.

5. The method of claim 1, wherein said movable applicator is automated.

6. The method of claim 1, wherein said plurality of tests is run with the aid of a control system.

7. The method of claim 6, wherein said control system is capable of carrying out at least one of:
   (a) scheduling;
   (b) recording data;
   (c) altering at least one parameter during a run;
   (d) storing data;
   (e) analyzing data.

8. The method of claim 7, wherein said at least one parameter is selected from the group consisting of flow rate of test material, start time of test material application, stop time of test material application, duration of introduction of test material, recovery period of test subject, name of control material, concentration of control material, control repetition interval, digital sampling rate, temperature of said test subject, and electrophysiological holding potential.

9. The method of claim 7, wherein said control system identifies the condition of said test subject.

10. The method of claim 1, wherein said at least one test subject is introduced by means of a movable applicator.

11. The method of claim 10, wherein said movable applicator is automated.

12. The method of claim 1, further including the step of removing said at least one test subject from each of said plurality of recording stations.

13. The method of claim 1, wherein said plurality of tests is run in sequence.

14. The method of claim 1, wherein said plurality of tests is run concurrently.

15. A method for running a plurality of tests to obtain electrophysiological data, the method comprising the steps of:
   (a) providing a plurality of recording stations, each of said recording stations capable of containing at least one test subject;
   (b) introducing at least one test subject into a first one of said plurality of recording stations;
   (c) introducing at least one test subject into a second one of said plurality of recording stations;
   (d) assessing the viability of said at least one test subject in said first one of said plurality of recording stations;

(e) assessing the viability of said at least one test subject in said second one of said plurality of recording stations;

(f) introducing at least one test material into at least one of said plurality of recording stations that contains a viable test subject as determined by the assessment made in steps (d) and (e), wherein a movable applicator introduces said at least one test material of step (f) directly into at least one of said plurality of recording stations;

(g) replacing said at least one test subject in said first one of said plurality of recording stations if said at least one test subject in said first one of said plurality of recording stations fails to respond adequately to a control or if the electrophysiological data of said at least one test subject in said first one of said plurality of recording stations exceeds a user-defined set point;

(h) replacing said at least one test subject in said second one of said plurality of recording stations if said at least one test subject in said second one of said plurality of recording stations fails to respond adequately to a control or if the electrophysiological data of said at least one test subject in said second one of said plurality of recording stations exceeds a user-defined set point; and (i) collecting said electrophysiological data from each of said plurality of tests, wherein the steps (b), (c), (d), (e), (f), (g), (h), and (i) are carried out without substantial intervention by a human operator, further including the step of disabling said second one of said recording stations if said second one of said recording stations has a higher than expected number of failures, the expected number of failures being defined by the user.

16. The method of claim 15, wherein each of said recording stations comprises:
(a) a holder for said test subject;
(b) a means for measuring the electrical response of said test subject to said at least one test material.

17. The method of claim 16, wherein each of said recording stations further includes a controller for controlling the electrical environment of said test subject.

18. The method of claim 15, wherein said at least one test material is introduced by means of a fluid stream.

19. The method of claim 15, wherein said movable applicator is automated.

20. The method of claim 15, wherein said plurality of tests is run with the aid of a control system.

21. The method of claim 20, wherein said control system is capable of carrying out at least one of:
(a) scheduling;
(b) recording data;
(c) altering at least one parameter during a run;
(d) storing data;
(e) analyzing data.

22. The method of claim 21, wherein said at least one parameter is selected from the group consisting of flow rate of test material, start time of test material application, stop time of test material application, duration of introduction of test material, recovery period of test subject, name of control material, concentration of control material, control repetition interval, digital sampling rate, temperature of said test subject, and electrophysiological holding potential.

23. The method of claim 21, wherein said control system identifies the condition of said test subject.

24. The method of claim 15, wherein said at least one test subject is introduced by means of a movable applicator.

25. The method of claim 24, wherein said movable applicator is automated.

26. The method of claim 15, further including the step of removing said at least one test subject from each of said plurality of recording stations.

27. The method of claim 15, wherein said plurality of tests is run in sequence.

28. The method of claim 15, wherein said plurality of tests is run concurrently.

* * * * *